United States Patent
Arnold et al.

(12) 
(10) Patent No.: US 6,174,922 B1
(45) Date of Patent: Jan. 16, 2001

(54) SULPHONAMIDE DERIVATIVES

(75) Inventors: Macklin Brian Arnold, Morgantown; Paul Leslie Ornstein, Carmel; Dennis Michael Zimmerman, Zionsville, all of IN (US); Ana Maria Escribano, Madrid (ES)

(73) Assignee: Eli Lilly and Company, Indianapolis, IN (US)

( * ) Notice: Under 35 U.S.C. 154(b), the term of this patent shall be extended for 0 days.

(21) Appl. No.: 09/251,058

(22) Filed: Feb. 23, 1999

Related U.S. Application Data

(60) Provisional application No. 60/075,701, filed on Feb. 24, 1998.

(51) Int. Cl.⁷ .......................... A61K 31/18; A61K 31/19; A61K 31/24; A61K 31/275
(52) U.S. Cl. .......................... 514/604; 548/205; 548/561; 548/569; 549/78; 549/265; 549/491; 556/489; 558/408; 558/413; 558/430; 560/12; 562/430; 564/80; 564/82; 564/85; 564/86; 564/89; 564/90

(58) Field of Search .................................... 514/63, 238.2, 514/255, 336, 357, 365, 427, 428, 438, 462, 471, 519, 523, 524, 538, 562, 601, 602, 603, 604, 810, 811, 812, 813; 544/383, 160; 546/280.4, 338; 548/205, 561, 569; 549/78, 265, 491; 556/489; 558/408, 413, 430; 560/12; 562/430; 564/80, 82, 85, 86, 89, 90

(56) References Cited

PUBLICATIONS

Nakao et al. Chem Abst # 90: 168635, 1979.*

* cited by examiner

*Primary Examiner*—Peter O'Sullivan
(74) *Attorney, Agent, or Firm*—Nelson L. Lentz

(57) ABSTRACT

The present invention provides novel sulphonamide derivatives which are useful for potentiating glutamate receptor function in a mammal requiring treatment, processes for their preparation, and pharmaceutical compositions containing them.

23 Claims, No Drawings

SULPHONAMIDE DERIVATIVES

This application claims the benefit of U.S. Provisional Application No. 60/075,701, filed Feb. 24, 1998.

FIELD OF THE INVENTION

The present invention relates to novel sulphonamide derivatives, to processes for their preparation, to pharmaceutical compositions containing them, and to their use as potentiators of glutamate receptor function.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2- 0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are unknown.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron.* Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulphonamides, S-oxides and homologs which are said to potentiate membrane currents induced by kainic acid and AMPA.

Ampakines have been shown to improve memory in a variety of animal tests. Staubli et al., *Proc. Natl. Acad. Sci.*, Vol. 91, pp 777–781, 1994, *Neurobiology*, and Arai et al., *The Journal of Pharmacology and Experimental Therapeutics*, 278: 627–638, 1996.

It has now been found that cyclothiazide and certain novel sulphonamide derivatives potentiate agonist-induced excitability of human GluR4B receptor expressed in HEK 293 cells. Since cyclothiazide is known to potentiate glutamate receptor function in vivo, it is believed that this finding portends that the sulphonamide derivatives will also potentiate glutamate receptor function in vivo, and hence that the compounds will exhibit ampakine-like behavior.

SUMMARY OF THE INVENTION

Accordingly, the present invention provides a compound of formula I:

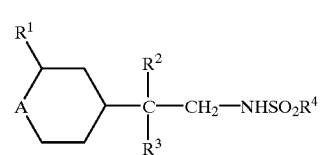

in which:

A represents $CR^5(X^1R^6)$ or $C=NO(CH_2)_nR^7$;

$R^1$ represents hydrogen, or together with $R^5$ a bond;

$R^2$ and $R^3$ each independently represents hydrogen or (1–4C)alkyl, or together with the carbon atom to which they are attached form a (3–6C)cycloalkyl ring;

$R^4$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group;

$R^5$ represents hydrogen, hydroxy, (1–4C)alkoxy, (1–4C)alkoxycarbonyl, or together with a substituent on $R^6$ a bond, or together with $R^1$ a bond;

$X^1$ represents a bond, or when $R^1$ represents hydrogen, NHCO;

$R^6$ represents (3–8C)cycloalkyl or an unsubstituted or substituted aromatic or heteroaromatic group;

n is an integer of from 1 to 4; and $R^7$ is as defined for $R^6$;

or a pharmaceutically acceptable salt thereof.

The present invention further provides compounds of the formula XVII:

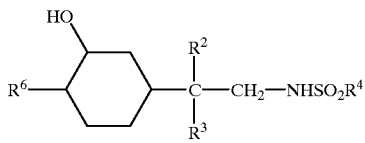

XVII in which:

$R^2$ and $R^3$ each independently represents hydrogen or (1–4C)alkyl, or together with the carbon atom to which they are attached form a (3–6C)cycloalkyl ring;

$R^4$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; and $R^6$ represents (3–8C)cycloalkyl or an unsubstituted or substituted aromatic or heteroaromatic group;

or a pharmaceutically acceptable salt thereof.

According to another aspect, the present invention provides a method of potentiating glutamate receptor function in a mammal requiring treatment, which comprises administering an effective amount of a compound of formula I or formula XVII, or a pharmaceutically acceptable salt thereof.

According to another aspect, the present invention provides the use of a compound of formula I or formula XVII, or a pharmaceutically acceptable salt thereof as defined hereinabove for the manufacture of a medicament for potentiating glutamate receptor function.

According to yet another aspect, the present invention provides the use of a compound of formula I or formula XVII or a pharmaceutically acceptable salt thereof as defined hereinabove for potentiating glutamate receptor function.

DETAILED DESCRIPTION OF THE INVENTION

In this specification, the term "potentiating glutamate receptor function" refers to any increased responsiveness of glutamate receptors, for example AMPA receptors, to glutamate or an agonist, and includes but is not limited to inhibition of rapid desensitisation or deactivation of AMPA receptors to glutamate.

A wide variety of conditions may be treated or prevented by the compounds of formula I or formula XVII and their pharmaceutically acceptable salts through their action as potentiators of glutamate receptor function. Such conditions include those associated with glutamate hypofunction, such as psychiatric and neurological disorders, for example cognitive disorders; neuro-degenerative disorders such as Alzheimer's disease; age-related dementias; age-induced memory impairment; movement disorders such as tardive dyskinesia, Hungtington's chorea, myoclonus and Parkinson's disease; sexual dysfunction; reversal of drug-induced states (such as cocaine, amphetamines, alcohol-induced states); depression; attention deficit disorder; attention deficit hyperactivity disorder; psychosis; cognitive deficits associated with psychosis; and drug-induced psychosis. The compounds of formula I or formula XVII may also be useful for improving memory (both short term and long term) and learning ability. The present invention provides the use of compounds of formula I or formula XVII for the treatment of each of these conditions.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I or of formula XVII can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. It is understood that all such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The designation "◀" refers to a bond that protrudes forward out of the plane of the page.

The designation "⦙⦙⦙" refers to a bond that protrudes backward out of the plane of the page.

For compounds of formula I in which A represents $CR^5(X^1R^6)$, preferably the group $R^5$ and the sulphonamide group are in a cis relationship as shown below. Such compounds are referred to hereinafter as the cis isomers.

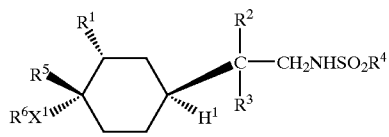

Mixtures of cis and trans isomers can be separated into the individual cis and trans isomers, which are included within the scope of the present invention, by one of ordinary skill in the art, using standard techniques and procedures such as reverse phase or normal phase high performance liquid chromatography or flash chromatography, with a suitable stationary phase and a suitable eluent. Examples of suitable stationary phases are silica gel, alumina, and the like. Examples of suitable eluents are ethyl acetate/hexane, ethyl acetate/toluene, methanol/dichloromethane, and the like.

It will be appreciated that when $R^5$ together with $R^1$ represents a bond, $X^1$ must represent a bond, and when $R^1$ represents hydrogen, $X^1$ may alternatively represent a bond or NHCO. Thus, it is understood that compounds of the formula Ia or formula Ib:

formula Ia
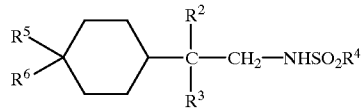

formula Ib
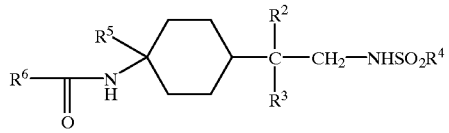

are included within the scope of formula I wherein the substituents are defined as hereinabove.

It will be appreciated that certain compounds of formula I or formula XVII possess an acidic or basic group, and may therefore form pharmaceutically acceptable salts with pharmaceutically acceptable bases or acids. Examples of pharmaceutically acceptable bases and acids include ammonia, alkali and alkaline earth metal hydroxides; inorganic acids such as hydrochloric, hydrobromic, hydriodic, sulfuric, and phosphoric acid, as well as organic acids such as para-toluenesulfonic, methanesulfonic, oxalic, para-bromophenyl-sulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, hippurate, butyne-1,4-dioate, hexane-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, naphthalene-2-sulfonate, mandelate, magnesium, tetramethylammonium, potassium, trimethylanm monium, sodium, methylammonium, calcium, and the like salts. It is understood that the above salts may form hydrates or exist in a substantially anhydrous form.

The term "treating" (or "treat") as used herein includes its generally accepted meaning which encompasses prohibiting, preventing, restraining, and slowing, stopping, or reversing progression, severity, or a resultant symptom.

As used herein, the term "aromatic group" means the same as aryl, and includes phenyl and a polycyclic aromatic carbocyclic ring such as naphthyl.

As used herein, the terms "Me", "Et", "Pr", "iPr", and "Bu" refer to a methyl, ethyl, propyl, isopropyl and butyl group respectively.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, triazolyl, tetrazolyl, pyridyl, pyridazinyl, pyrimidyl, benzofuryl, benzothienyl, benzimidazolyl, benzoxazolyl, benzothiazolyl, indolyl, quinolyl, indazole, and benzotriazole.

The term "substituted" as used in the term "substituted aromatic or heteroaromatic group" herein signifies that one or more (for example one or two) substituents may be present, said substituents being selected from atoms and groups which, when present in the compound of formula I or formula XVII, do not prevent the compound of formula I or formula XVII from functioning as a potentiator of glutamate receptor function.

Examples of substituents which may be present in a substituted aromatic or heteroaromatic group include halogen; amino; cyano; formyl; carboxy; nitro; (1–4C)alkyl; (2–4C)alkenyl; (2–4C)alkynyl; halo(1–4C)alkyl; cyano (1–4C)alkyl; amino(1–4C)alkyl; (1–4C)alkyl-$NHSO_2R^{17}$;

(1–4C)alkyl-CO$_2$R$^{18}$; (1–4C)alkyl-CO$_2$H; (1–4C)alkyl-CONR$^9$R$^{10}$; (3–8C)cycloalkyl; 2,5-dimethylpyrrolyl; wherein R$^{17}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, or NR$^9$R$^{10}$ in which each of R$^9$ and R$^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; R$^{18}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, and groups of formula (L$^1$)$_x$—X$^2$—(L$^1$)$_y$—R$^{11}$ in which each of L$^1$ and L$^2$ independently represents (1–4C)alkylene, one of x and y is 0 and the other is 0 or 1, X$^2$ represents a bond, O, S, NH, CO, CONH or NHCO, and R$^{11}$ represents a furyl, thienyl, thiazolyl, pyridyl or phenyl group which is unsubstituted or substituted by one or two of halogen, (1–4C)alkyl and (1–4C)haloalkyl.

The term (1–6C)alkyl includes (1–4C)alkyl. Particular values are methyl, ethyl, propyl, isopropyl, butyl, isobutyl, t-butyl, pentyl and hexyl.

The term (2–6C)alkenyl includes (3–6C)alkenyl and (2–4C)alkenyl. Particular values are vinyl and prop-2-enyl.

The term (2–6C)alkynyl includes (3–6C)alkynyl and (3–4C)alkynyl. A particular value is prop-2-ynyl.

The term (3–8C)cycloalkyl includes (3–6C)cycloalkyl. Particular values include cyclopropyl, cyclobutyl, cyclopentyl and cyclohexyl.

The term halogen includes fluorine, chlorine, bromine and iodine.

The term halo(1–6C)alkyl includes fluoro(1–6C)alkyl, such as trifluoromethyl and 2,2,2-trifluoroethyl, and chloro(1–6C)alkyl such as chloromethyl.

The term (2–4C)alkylene includes ethylene, propylene and butylene. A preferred value is ethylene.

The term (1–4C)alkylphenyl includes the following:

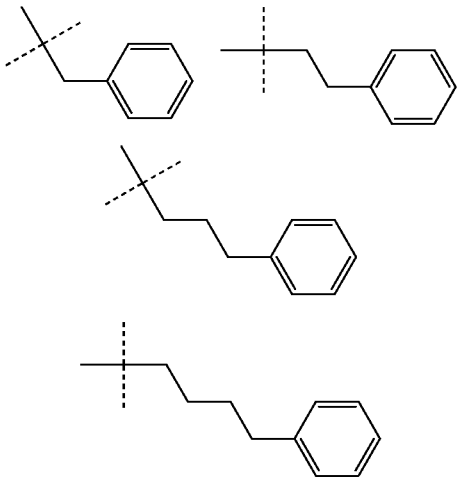

The term thienyl includes thien-2-yl and thien-3-yl.
The term furyl includes fur-2-yl and fur-3-yl.
The term oxazolyl includes oxazol-2-yl, oxazol-4-yl and oxazol-5-yl.

The term isoxazolyl includes isoxazol-3-yl, isoxazol-4-yl and isoxazol-5-yl.

The term oxadiazolyl includes [1,2,4]oxadiazol-3-yl and [1,2,4]oxadiazol-5-yl.

The term pyrazolyl includes pyrazol-3-yl, pyrazol-4-yl and pyrazol-5-yl.

The term thiazolyl includes thiazol-2-yl, thiazol-4-yl and thiazol-5-yl.

The term thiadiazolyl includes [1,2,4]thiadiazol-3-yl, and [1,2,4]thiadiazol-5-yl.

The term isothiazolyl includes isothiazol-3-yl, isothiazol-4-yl and isothiazol-5-yl.

The term imidazolyl includes imidazol-2-yl, imidazolyl-4-yl and imidazolyl-5-yl.

The term triazolyl includes [1,2,4]triazol-3-yl and [1,2,4]triazol-5-yl.

The term tetrazolyl includes tetrazol-5-yl.

The term pyridyl includes pyrid-2-yl, pyrid-3-yl and pyrid-4-yl.

The term pyridazinyl includes pyridazin-3-yl, pyridazin-4-yl, pyridazin-5-yl and pyridazin-6-yl.

The term pyrimidyl includes pyrimidin-2-yl, pyrimidin-4-yl, pyrimidin-5-yl and pyrimidin-6-yl.

The term benzofuryl includes benzofur-2-yl and benzofur-3-yl.

The term benzothienyl includes benzothien-2-yl and benzothien-3-yl.

The term benzimidazolyl includes benzimidazol-2-yl.
The term benzoxazolyl includes benzoxazol-2-yl.
The term benzothiazolyl includes benzothiazol-2-yl.
The term indolyl includes indol-2-yl and indol-3-yl.
The term quinolyl includes quinol-2-yl.

In the compounds of formula I or formula XVII, preferably R$^2$ and R$^3$ each independently represents hydrogen or methyl. More preferably R$^2$ represents methyl and R$^3$ represents hydrogen.

R$^4$ preferably represents ethyl, isopropyl or dimethylamino. More preferably R$^4$ represents isopropyl.

In the compounds of formula I, R$^5$ preferably represents hydrogen, hydroxy or together with R$^1$ a bond.

In the compounds of formula I or formula XVII, R$^6$ preferably represents cyclopentyl, or a furyl, thienyl, thiazolyl, pyridyl or phenyl group which is unsubstituted or substituted with one or two substituents selected independently from halogen; amino; cyano; formyl; carboxy; nitro; (1–4C)alkyl; (2–4C)alkenyl; (2–4C)alkynyl; halo(1-4C)alkyl; cyano(1–4C)alkyl; amino(1–4C)alkyl; (1–4C)alkyl-NHSO$_2$R$^{17}$; (1–4C)alkyl-CO$_2$R$^{18}$; (1–4C)alkyl-CO$_2$H; (1–4C)alkyl-CONR$^9$R$^{10}$; (3–8C)cycloalkyl; 2,5-dimethylpyrrolyl; wherein R$^{17}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, or NR$^9$R$^{10}$ in which each of R$^9$ and R$^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; R$^{18}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, and groups of formula (L$^1$)$_x$—X$^2$—(L$^1$)$_y$—R$^{11}$ in which each of L$^1$ and L$^2$ independently represents (1–4C)alkylene, one of x and y is 0 and the other is 0 or 1, $X^2$ represents a bond, O, S, NH, CO, CONH or NHCO, and $R^{11}$ represents a furyl, thienyl, thiazolyl, pyridyl or phenyl group which is unsubstituted or substituted by one or two of halogen, (1–4C)alkyl and (1–4C)haloalkyl.

More preferably, $R^6$ represents

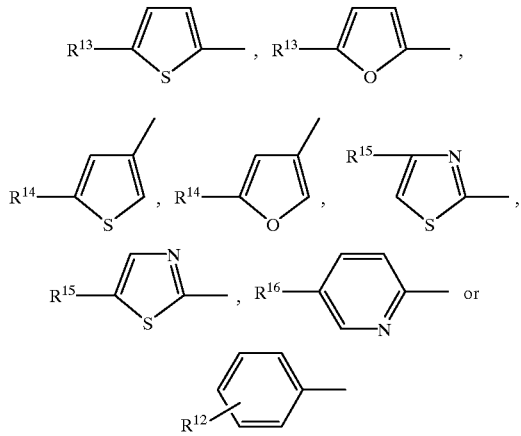

in which $R^{12}$, $R^{13}$, $R^{14}$, $R^{15}$ and $R^{16}$ represent halogen, amino, cyano, formyl, nitro, (1–4C)alkyl, (2–4C)alkenyl, (2–4C)alkynyl, halo(1–4C)alkyl, cyano(1–4C)alkyl, amino (1–4C)alkyl; (1–4C)alkyl-$NHSO_2R^{17}$, (3–8C)cycloalkyl, wherein $R^{17}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C) alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; or a group of formula $(L^1)_x$—$X^2$—$(L^1)_y$—$R^{11}$.

Most especially preferred, $R^6$ represents:

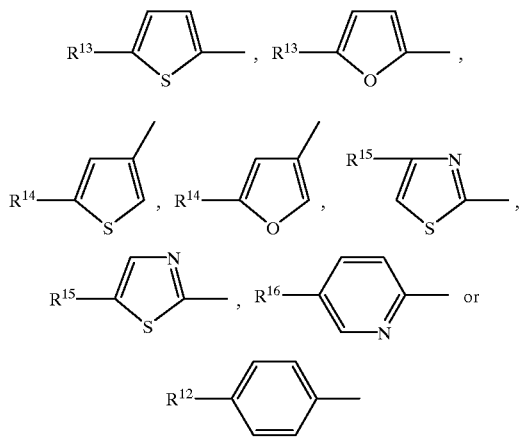

in which $R^{12}$, $R^{13}$, $R^{14}$, $R^{15}$ and $R^{16}$ represent halogen, amino, cyano, formyl, nitro, (1–4C)alkyl, (2–4C)alkenyl, (2–4C)alkynyl, halo(1–4C)alkyl, cyano(1–4C)alkyl, amino (1–4C)alkyl; (1–4C)alkyl-$NHSO_2R^{17}$, (3–8C)cycloalkyl, wherein $R^{17}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C) alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; or a group of formula $(L^1)_x$—$X^2$—$(L^1)_y$—$R^{11}$.

Examples of particular values for $R^6$ are cyclopentyl, thien-2-yl, thien-3-yl, fur-3-yl, 5-(pyrid-2-yl)thien-2-yl, thiazol-2-yl, pyrid-2-yl, phenyl, 4-formylphenyl, 4-aminophenyl, 4-cyanophenyl, 4-cyanomethylphenyl, 4-aminomethylphenyl, 4-methylsulfonylaminoethylphenyl, 4-isopropylsulfonyl-aminomethylphenyl, or 4-(2,5-dimethylpyrrolyl)phenyl; or together with $R^5$ and the carbon atom to which it is attached is spiroisobenzofuranyl.

In formula I, an example of a particular value for $R^7$ is phenyl.

Preferably A represents $CR^5(X^1R^6)$.

According to another aspect, the present invention provides a process for the preparation of a compound of formula I, or a pharmaceutically acceptable salt thereof, which comprises:

(a) reacting a compound of formula

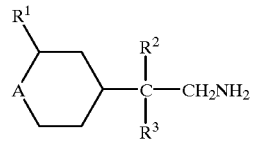

II with a compound of formula $R^4SO_2Z^1$  III in which $Z^1$ represents a leaving atom or group; or (b) for a compound of formula I in which A represents $CR^5(X^1R^6)$, $R^5$ represents hydroxyl and $X^1$ represents a bond, reacting a compound of formula

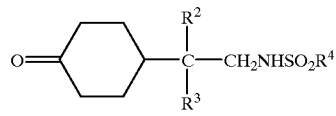

IV with a compound of formula $R^6Z^2$  V in which $Z^2$ represents an alkali or alkaline earth residue; or (c) for a compound of formula I in which A represents C=NO$(CH_2)_nR^7$, reacting a compound of formula IV with a compound of formula $R^7(CH_2)_nONH_2$  VI (d) for a compound of formula I in which A represents $CR^5(X^1R^6)$, and $R^5$ together with $R^1$ represents a bond, dehydrating a compound of formula

VII

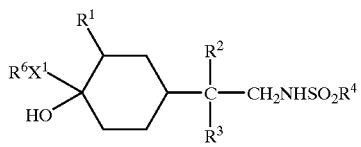

(e) for a compound of formula I in which A represents $CR^5(X^1R^6)$, $X^1$ represents a bond, and $R^5$ together with $R^1$ represents a bond, reacting a compound of formula

VIII

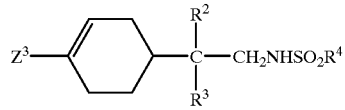

in which $Z^3$ represents a leaving atom or group with a compound of formula $$R^6M \qquad IX$$

in which M is $B(OH)_2$, Br, I, or ZnY and Y is a halogen atom; or alternatively reacting a compound of formula VIII with a trialkyltin reagent;
(f) for a compound of formula I in which A represents $CR^5(X^1R^6)$, $R^1$ represents hydrogen and $R^5$ represents hydrogen, reducing a compound of formula VII;
(g) for a compound of formula I in which A represents $CR^5(X^1R^6)$, and $X^1$ represents NHCO, reacting a compound of formula

X

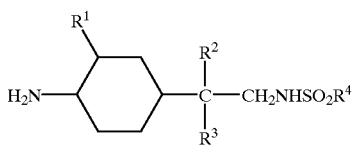

with a compound of formula $$R^6COZ^4 \qquad XI$$

in which $Z^4$ represents a leaving atom or group; followed, if desired, by forming a pharmaceutically acceptable salt.

In step (a) of the process according to the invention, the leaving atom or group represented by $Z^1$ may be, for example, a halogen atom such as a chlorine or bromine atom.

The reaction is conveniently performed in the presence of a base, for example as alkali metal hydroxide such as sodium hydroxide, or a tertiary amine, such as triethylamine or 1,8-diazabicyclo[5.4.0]undec-7-ene. Suitable solvents include halogenated hydrocarbons, such as dichloromethane. The reaction is conveniently performed at a temperature in the range of from $-20$ to $100°$ C., preferably from $-5$ to $50°$ C.

In step (b) of the process according to the invention, the alkali metal residue represented by $Z^2$ may be, for example, lithium. The process is conveniently performed under an inert atmosphere and at a temperature in the range of from $-78$ to $25°$ C. Suitable solvents include ethers, such as tetrahydrofuran or diethyl ether.

The compounds of formula IV may be prepared by hydrolyzing a ketal of formula

XII

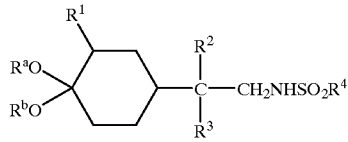

in which each of $R^a$ and $R^b$ represents a (1–6C)alkyl group or together represent a (2–4C)alkylene chain. The hydrolysis is conveniently performed in the presence of hydrochloric acid at ambient temperature.

The compounds of formula XII may be prepared by reacting a compound of formula

XIII

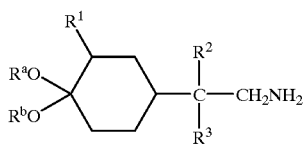

with a compound of formula III.

The reaction is conveniently performed according to the method of step (a) as described hereinabove.

The compounds of formula XIII may be prepared by reducing a nitrile of formula

XIV

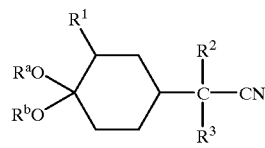

The reduction is conveniently performed using a hydride reducing agent such as lithium aluminum hydride. Suitable solvents include ethers such as diethyl ether or tetrahydrofuran.

Compounds of formula XIV in which $R^2$ and $R^3$ each represents hydrogen may be converted into compounds of formula XIV in which one or both of $R^2$ and $R^2$ represents (1–4C)alkyl by reaction with a (1–4C)alkyl halide in the presence of a strong base such as lithium bis(trimethylsilyl) amide. Convenient solvents include ethers, such as tetrahydrofuran.

The compounds of formula XIV in which $R^2$ and $R^3$ each represents hydrogen may be prepared by reacting a 1,4-cyclohexanedione monoketal, such as 1,4-cyclohexanedione monoethylene ketal, with a dialkyl (cyanomethyl) phosphonate, such as diethyl (cyanomethyl)phosphonate, in the presence of a strong base, such as sodium hydride, followed by reduction, for example by catalytic hydrogenation in the presence of palladium on carbon. Suitable solvents for the first step include ethers, such as tetrahydrofuran. Suitable solvents for the reduction step include alcohols, such as ethanol.

Step (c) of the process according to the invention is conveniently performed at a temperature in the range of from $-10$ to $120°$ C. Suitable solvents include halogenated hydrocarbons, such as dichloromethane.

The dehydration of a compound of formula VII according to step (d) of the process is conveniently performed by heating, for example to a temperature in the range of from 40 to 100° C. Suitable solvents include halogenated hydrocarbons, such as dichloromethane.

In step (e) of the process according to the invention, the leaving atom or group represented by $Z^3$ may be, for example, an organosulfonyloxy group, such as trifluoromethylsulfonyloxy or a trialkyltin, such as $(Me)_3Sn$ or $(Bu)_3Sn$. The halogen atom represented by Y may be, for example, a bromine atom. The reaction is conveniently performed in the presence of a tetrakis(triarylphosphine) palladium halide catalyst, such as tetrakis(triphenylphosphine)palladium chloride, and a base, such as potassium carbonate. Convenient solvents for the reaction include ethers, such as dioxane or tetrahydrofuran. The temperature at which the reaction is conducted is preferably in the range of from 0 to 150° C., preferably 75 to 120° C.

The compounds of formula VIII in which $Z^3$ represents an organosulfonyloxy group may be prepared by reacting a compound of formula IV with an N-arylsulfonimide, such as N-phenyltrifluoromethane sulfonimide. The reaction is conveniently performed in the presence of a strong base, such as lithium bis(trimethylsilyl)amide. Convenient solvents include ethers, such as tetrahydrofuran. The reaction is conveniently performed at from −100 to −50° C.

The compounds of formula VII may be reduced according to step (f) of the process by reaction with a reducing agent, such as a trialkylsilane, for example triethylsilane, and boron trifluoride, conveniently as the diethyl etherate. The reaction is conveniently performed at a temperature of from −100 to −50° C. Convenient solvents includes halogenated hydrocarbon, such as dichloromethane.

Alternatively, the compounds of formula VII may be reduced with a reducing agent such as borane dimethylsulfide complex. For example, compound VII is dissolved in a suitable organic solvent, such as tetrahydrofuran and heated to reflux. To the refluxing solution is added about 1.1 equivalents of borane dimethylsulfide via syringe. The mixture is heated at reflux for about 60 minutes and then cooled to room temperature. The reaction mixture is then treated with 6N HCl and then refluxed for about 60 minutes. The reaction mixture is again cooled to room temperature and the pH is adjusted to about pH 10 with 5N NaOH. The reaction mixture is then diluted with water and extracted with a suitable organic solvent, such as dichloromethane. The organic extracts are combined, dried over anhydrous sodium sulfate, filtered and concentrated under vacuum to provide the reduced compound.

In process step (g), the leaving atom or group $Z^4$ may be, for example, a halogen atom such as a chlorine atom. The reaction is conveniently performed in the presence of a base, for example a tertiary amine such as triethylamine, and at a temperature in the range of from 0 to 100° C. Convenient solvents include halogenated hydrocarbons, such as dichloromethane.

The compounds of formula X may be prepared by reducing a compound of formula

XV

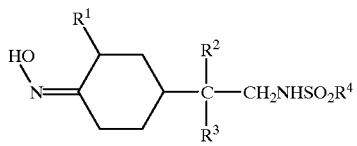

The reduction is conveniently performed using a hydride reducing agent, for example lithium aluminum hydride, and at a temperature of from 0 to 100° C. Convenient solvents include ethers such as diethyl ether.

The compounds of formula II, used as starting materials in step (a), may be prepared by a process analogous to steps (b) to (g), but using a protected amino compound (for example, an N-acetyl compound) in place of a sulphonamide, and then removing the protecting group (for example by acid-catalyzed hydrolysis).

The compounds of formula XVII:

XVII

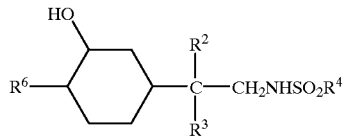

may be prepared from compounds of formula XVI:

XVI

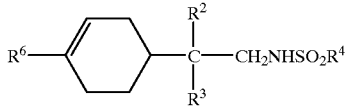

under conditions well known in the art. For example, a compound of formula XVI is dissolved in a suitable organic solvent, such as tetrahydrofuran, cooled to about 0° C. and treated with a suitable borane reducing agent, such as borane dimethyl sulfide complex. The reaction mixture is stirred for about 4 hours at 0° C. and then slowly quenched with ethanol. The solution is maintained at about 0° C. and 3N aqueous sodium hydroxide is added followed by 30% hydrogen peroxide. The reaction mixture is then stirred for about one hour at 0° C. The compound of formula XVII is then isolated and purified by techniques well know in the art such as extraction techniques and flash chromatography. For example, the organic layer is separated and the aqueous layer is extracted with a suitable organic solvent, such as diethyl ether. The organic layer and extracts are then combined, dried over anhydrous magnesium sulfate, filtered and concentrated under vacuum. The crude material can then be purified by flash chromatography on silica gel with a suitable eluent, such as ethyl acetate/hexane to provide purified XVII.

More specifically, compounds of formulas XIX and XX can be prepared as shown in Scheme I. Reagents and starting materials are readily available to one of ordinary skill in the art. All substituents, unless otherwise specified, are previously defined.

Scheme I

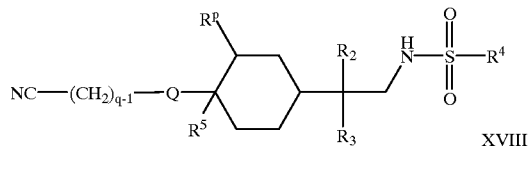

XVIII

Step A

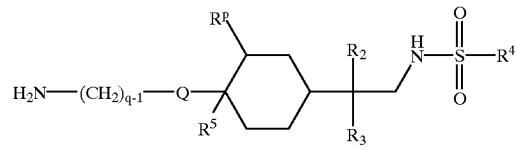

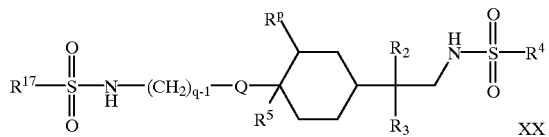

In Scheme I, step A the compound of formula XVIII wherein Q represents a (3–8C)cycloalkyl, an aromatic group, unsubstituted or substituted, such as phenyl, or a heteroaromatic group, unsubstituted or substituted, and $R^P$ represents hydrogen, hydroxy, or together with $R^5$ a bond, q is an integer 1, 2, 3 or 4, and the remaining substituents are defined as hereinabove, is converted to the amine of formula XIX under conditions well known in the art. For example, compound XVIII is dissolved in a suitable organic solvent, such as tetrahydrofuran and heat to reflux. To the refluxing solution is added about 1.1 equivalents of a borane reagent, such as borane dimethylsulfide complex. The reaction mixture is then heated at reflux for about 1 to 2 hours, cooled to room temperature and then treated with 6N HCl. The reaction is again heated at reflux for about 1 hour, cooled and the pH is adjusted to about pH 10 with aqueous sodium hydroxide. The product, compound XIX, is then isolated and purified by standard techniques such as extraction and chromatography.

For example, the reaction mixture is diluted with water and extracted with a suitable organic solvent, such as dichloromethane. The organic extracts are combined, dried over anhydrous magnesium sulfate, filtered and concentrated under vacuum to provide compound XIX.

In Scheme I, step B compound XIX is sulfonylated to provide the compound of formula XX under conditions well known in the art. For example, compound XIX is dissolved in a suitable organic solvent, such as dichloromethane, followed by addition of about 1.05 equivalents of triethylamine. The solution is cooled to about 0° C. and treated with about 1.05 equivalents of a suitable sulfonyl chloride of formula $R^{17}SO_2Cl$, such as methanesulfonyl chloride. The reaction is then allowed to warm to room temperature over 2 hours with stirring. The product, compound XX, is then isolated and purified using techniques well known to one of ordinary skill in the art, such as extraction and chromatography.

For example, the reaction mixture is then diluted with a suitable organic solvent, such as dichloromethane and 10% aqueous sodium bisulfate. The organic layer is separated and the aqueous layer is extracted with dichloromethane. The organic layer and extracts are then combined, dried over anhydrous sodium sulfate, filtered and concentrated under vacuum to provide compound XX. Compound XX can then be purified by flash chromatography on silica gel with a suitable eluent, such as ethyl acetate/hexane to provide purified compound XX.

Compounds of formulas XXI and XXII can be prepared as disclosed in Scheme II. The reagents and starting materials are readily available to one of ordinary skill in the art.

All substituents, unless otherwise specified, are previously defined.

Scheme II

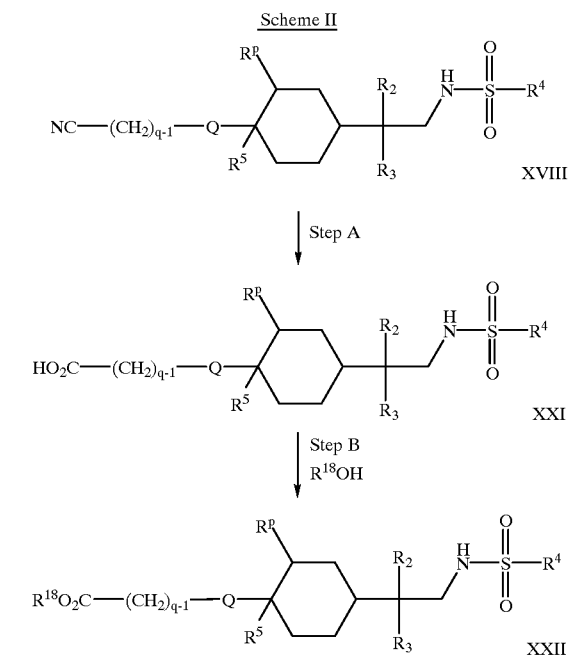

In Scheme II, step A the compound of formula XVIII can be hydrolyzed under standard conditions to provide the compound of formula XXI. For example, compound XVIII is dissolved in a suitable organic solvent, such as dioxane and treated with a suitable base, such as sodium hydroxide. The reaction mixture is then heated at about 100° C. for about 24 hours. The reaction mixture is then cooled to room temperature and acidified with 10t sodium bisulfate. Compound XXI is then isolated and purified by techniques well known in the art, such as extraction and chromatography.

For example, the reaction mixture is extracted with a suitable organic solvent, such as ethyl acetate, the organic extracts are combined, dried over anhydrous magnesium sulfate, filtered and concentrated under vacuum to provide compound XXI. Compound XXI can be purified by flash chromatography on silica gel with a suitable eluent, such as methanol/chloroform.

In Scheme II, step B the compound of formula XXI can be esterified under conditions well known in the art to provide the compound of formula XXII. For example, compound XXI is dissolved in a suitable alcoholic organic solvent of formula $R^{18}OH$, such as ethanol and HCl gas is bubbled through the solution until the mixture is saturated. The reaction mixture is then heated at 60° C. for about 24 hours, then cooled to room temperature and concentrated under vacuum. Additional ethanol is added to the residue and the mixture is again concentrated under vacuum to provide the ethyl ester of compound XXII. Compound XXII can be then be purified by flash chromatography on silica gel with a suitable eluent, such ethyl acetate/hexane.

Compounds of formula XXIII can be prepared as disclosed in Scheme III. Starting material and reagents are readily available to one ordinary skill in the art. All substituents, unless otherwise specified, are previously defined.

Scheme III

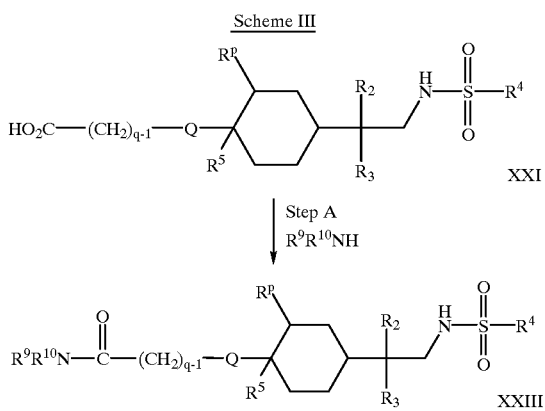

In Scheme III, step A compound XXI is readily comverted to the amide of formula XXIII under conditions well known in the art. For example, compound XXI is dissolved in a suitable organic solvent, such as tetrahydrofuran and treated with an excess of thionyl chloride. The reaction mixture is stirred at room temperature for about 16 hours and then concentrated under vacuum. The residue is then dissolved in a suitable organic solvent, such as methylene chloride. The solution is added to a solution of one equivalent of a suitable amine of formula $R^9R^{10}NH$, such as dimethylamine in dichloromethane with stirring. The mixture is stirred for about 2 hours at about 0° C. and then 10% aqueous sodium bisulfate is added. Compound XXIII is then isolated and purified by techniques well known in the art, such as extraction and flash chromatography.

For example, the reaction mixture is then extracted with a suitable organic solvent, such as methylene chloride, the organic extracts are combined, dried over anhydrous sodium sulfate, filtered and concentrated under vacuum to provide compound XXIII. This can then be purified by flash chromatography on silica gel with a suitable eluent, such as ethyl acetate/hexane to provide the purified compound XXIII.

Some of the intermediates disclosed herein, for example the compounds of formula IV, are novel and are provided as further aspects of the invention.

The ability of compounds of formula I or formula XVII to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK cells stably expressing human GluR4B (obtained as described in European Patent Application Publication Number EP-A1-583917) are prepared. The tissue culture medium in the wells is then discarded, and the wells are each washed once with 200 μl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 μM Fluo3-AM dye (obtained from Molecular Probes Inc., Eugene, Oreg.) in buffer in each well. After the incubation, each well is washed once with 100 μl buffer, 200 μl of buffer is added and the plates are incubated for 30 minutes.

Solutions for use in the test are also prepared as follows. 30 μM, 10 μM, 3 μM and 1 μM dilutions of test compound are prepared using buffer from a 10 mM solution of test compound in DMSO. 100 μM cyclothiazide solution is prepared by adding 3 μl of 100 mM cyclothiazide to 3 ml of buffer. Control buffer solution is prepared by adding 1.5 μl DMSO to 498.5 μl of buffer.

Each test is then performed as follows. 200 μl of control buffer in each well is discarded and replaced with 45 μl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 μl of buffer and 45 μl of test compound in buffer in appropriate wells. A second fluorescent reading is taken after 5 minutes incubation. 15 μl of 400 μM glutamate solution is then added to each well (final glutamate concentration 100 μM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 μM cyclothiazide.

In another test, HEK293 cells stably expressing human GluR4 (obtained as described in European Patent Application Publication No. EP-A1-0583917) are used in the electro-physiological characterization of AMPA receptor potentiators. The extracellular recording solution contains (in mM) 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis (oxyethylene-nitrilo)tetraacetic acid), pH=7.2 with CsOH, 295 mOsm kg-1. With these solutions, recording pipettes have a resistance of 2–3 MΩ. Using the whole-cell voltage clamp technique (Hamill et al.(1981)Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM, they produce a greater than 30% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or formula XVII or a pharmaceutically acceptable salt thereof as defined hereinabove and a pharmaceutically acceptable diluent or carrier.

As used herein the term "mammal" refers to a mouse, guinea pig, rat, dog, human and the like. It is understood that the preferred mammal is a human.

As used herein the term "effective amount" refers to the amount or dose of the compound which provides the desired effect in the mammal under diagnosis or treatment.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

|  | Quantity (mg/capsule) |
| --- | --- |
| Formulation 1 Hard gelatin capsules are prepared using the following ingredients | |
| Active Ingredient | 250 |
| Starch, dried | 200 |
| Magnesium stearate | 10 |
| Total | 460 mg |

The above ingredients are mixed and filled into hard gelatin capsules in 460 mg quantities.

| Formulation 2 Tablets each containing 60 mg of active ingredient are made as follows | |
| --- | --- |
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The following Preparations and Examples illustrate the invention. These Preparations and Examples are understood to be illustrative only and are not intended to limit the scope of the present invention in any way. The reagents and starting materials are readily available to one of ordinary skill in the art. In the Preparations and Examples, the following abbreviations are used: THF, tetrahydrofuran.

Preparation 1

N-[2-[1,4-dioxaspiro[4.5]dec-8-yl]propyl] 2-propanesulfonamide

A. 1,4-dioxaspiro[4.5]dec-8-ylidene acetonitrile: To a suspension of 7.2 g (60% by weight in oil, 178 mmol) of sodium hydride (washed three times with hexane) in 200 ml of THF, was added 31.5 g (178 mmol) of diethyl (cyanomethyl)phosphonate neat at ambient temperature. The mixture was stirred for 30 min at ambient temperature and then 20 g (128 mmol) of 1,4-cyclohexanedione monoethylene ketal in 200 ml of THF was added. After 1 h, the reaction was quenched with $NH_4Cl$ saturated solution and extracted three times with ethyl acetate. The organic phase was dried over $Na_2SO_4$, filtered and concentrated in vacuo. Chromatography (300 g of silica gel, 20% ethyl acetate/hexane) of the residue afforded 22.53 g (98%) of the title compound.

B. 1,4-dioxaspiro[4.5]dec-8-yl acetonitrile: A solution of 22.5 g (126 mmol) of material from step A in 430 ml of ethanol was hydrogenated with 2.25 g of 5% Pd/C at ambient temperature and 60 psi for 2h. The mixture was filtered through celite and concentrated in vacuo to afford 21.24 g (93%) of the title compound.

C. 2-[1,4-dioxaspiro[4.5]dec-8-yl] propanenitrile: To a solution of 21.24 g (117 mmol) of material from step B in 390 ml of THF at −78° C. was added 128 ml of a 1M solution of lithium bis(trimethylsilyl)amide in THF (128 mmol). The mixture was stirred for 30 min and then 18.17 g (128 mmol) of iodomethane was added at −78° C. The bath was removed and the mixture was stirred at ambient temperature for 1 h. The reaction was quenched with $NH_4Cl$ saturated solution and extracted three times with ethyl acetate. The organic phase was dried over $Na_2SO_4$, filtered and concentrated in vacuo. Chromatography (400 g of silica gel, 20% ethyl acetate/hexane) of the residue afforded 14.6 g (64%) of the title compound.

D. 2-[1,4-dioxaspiro[4.5]dec-8-yl] propylamine: To an ambient temperature suspension of 215 mg (5.66 mmol) of lithium aluminum hydride in 17 ml of diethyl ether was added dropwise 1.0 g (5.15 mmol) of material from step C in 7 ml of diethyl ether and 2 ml of THF. The mixture was stirred overnight. $Na_2SO_4 \cdot 10H_2O$ was added, and the mixture stirred for 30 min at ambient temperature. The solid was filtered and the organic solution was concentrated in vacuo.

E. N-[2-[1,4-dioxaspiro[4.5]dec-8-yl]propyl] 2-propanesulfonamide: A solution of the material from step D, 1.02 g, (5.15 mmol) in dichloromethane (17 ml) was cooled to 0° C., triethylamine 0.79 ml (5.67 mmol) was added, followed by isopropylsulfonyl chloride (0.64 ml, 5.67 mmol). The ice-bath was removed and the solution was stirred at ambient temperature for 2 h. The organic solution was washed with 1 N hydrochloric acid, sodium bicarbonate saturated solution, brine, dried over $Na_2SO_4$ filtered and concentrated in vacuo. Chromatography (100 g of silica gel, 33% ethyl acetate/hexane) of the residue afforded 431 mg (28% for steps D and E) of the title compound. Analysis calculated for $C_{14}H_{27}NO_4S$: % C, 55.05; % H, 8.91; % N, 4.59. Found: % C, 54.92; % H, 9.01; % N, 4.81. Field Desorption Mass Spectrum: M+1=306

Preparation 2
N-[2-[4-oxocyclohexyl]propyl] 2-propanesulfonamide

A solution of 250 mg (0.81 mmol) of the material from Preparation 1 in 3 ml of THF and 8.1 ml of a 1N hydrochloric acid solution was stirred overnight at ambient temperature. The mixture was washed with sodium bicarbonate saturated solution and extracted three times with diethyl ether. The organic phase was dried over $Na_2SO_4$, filtered and concentrated in vacuo. Chromatography (75 g of silica gel, 50% ethyl acetate/hexane) of the residue afforded 160 mg (75%) of the title compound. Analysis calculated for $C_{12}H_{23}NO_3S$: % C, 55.14; % H, 8.87; % N, 5.36. Found: % C, 55.53; % H, 8.67; % N, 4.95. Field Desorption Mass Spectrum: M+1=262

Preparation 3
N-[2-[4-hydroxycyclohexyl]propyl] 2-propanesulfonamide cis- and trans-isomers Prepared as in Example 6 using 1.2 ml of 2 M solution of cyclopentylmagnesium chloride in diethylether (2.4 mmol) and 250 mg (0.95 mmol) of material from Preparation 2 in 3 ml of THF/diethyl ether (1:1). Chromatography (50 g of silica gel, 50% ethyl acetate/hexane) of the residue afforded 128 mg (51%) of the title compound. Cis-Isomer: Analysis calculated for $C_{12}H_{25}NO_3S$: % C, 54.72; % H, 9.57; % N, 5.31. Found: % C, 54.43; % H, 9.27; % N, 5.19. Field Desorption Mass Spectrum: M=263. Trans-Isomer: Analysis calculated for $C_{12}H_{25}NO_3S$: % C, 54.72; % H, 9.57; % N, 5.31. Found: % C, 55.03; % H, 9.26; % N, 5.25. Field Desorption Mass Spectrum: M=263

Preparation 4
N-[2-[4-(hydroxyimino)cyclohexyl]propyl] 2-propanesulfonamide

A solution of 100 mg (0.38 mmol) of the material prepared in Preparation 2 in 2.5 ml of dichloromethane and 1.5 ml of methanol, 26 mg (0.38 mmol) of hydroxylamine hydrochloride and 60 mg (0.76 mmol) of pyridine was stirred for 3 days. 10 ml of water were added to the mixture and extracted three times with dichloromethane, dried over $Na_2SO_4$ filtered and concentrated in vacuo. Chromatography (75 g of silica gel, 50% ethyl acetate/hexane) of the residue afforded 39 mg (37%) of the title compound. Analysis calculated for $C_{12}H_{24}N_2O_3S$ $0.56H_2O$: % C, 50.31; % H, 8.84; % N, 9.78. Found: % C, 50.52; % H, 8.42; % N, 9.21. Field Desorption Mass Spectrum: M+1=277.

Preparation 5

N-[2-[1,4-dioxaspiro[4.5]dec-8-yl]ethyl] 2-propanesulfonamide

A. 2-[1,4-dioxaspiro[4.5]dec-8-yl] ethylamine A solution of 2 g (1.16 mmol) of material from Preparation 1, step A and 30 ml of anhydrous ammonia in 130 ml of ethanol and 70 ml of THF was hydrogenated with 0.2 g of Raney Nickel at 120° C. and 1000 psi for 12h. The mixture was filtered through celite and concentrated in vacuo to afford 1.96 g (95%) of the title compound.

B. N-[2-[1,4-dioxaspiro[4.5]dec-8-yl]ethyl] 2-propanesulfonamide: A solution of the material from step A, 1.96 g, (10.6 mmol) in dichloromethane (35 ml) was cooled to 0° C., 1,8-diazabicyclo[5.4.0]undec-7-ene 1.96 g (12.7 mmol) was added, followed by isopropylsulfonyl chloride (1.86 g, 3.35 mmol). The ice-bath was removed and the solution was stirred at ambient temperature overnight. The organic solution was washed with 1N hydrochloric acid, sodium bicarbonate saturated solution, brine, dried over $Na_2SO_4$ filtered and concentrated in vacuo. Afforded 2.1 g (68%) of the title compound. Ion Electrospray Mass Spectrum: M+1=292.

Preparation 6

N-[2-[4-oxocyclohexyl]ethyl] 2-propanesulfonamide

A solution of 290 mg (1.0 mmol) of the material from Preparation 5 in 5 ml of THF and 10 ml of a 1N hydrochloric acid solution was stirred overnight at ambient temperature. The mixture was washed with sodium bicarbonate saturated solution and extracted three times with diethyl ether. The organic phase was dried over $Na_2SO_4$, filtered and concentrated in vacuo. Afforded 240 mg (97%) of the title compound. Analysis calculated for $C_{11}H_{21}NO_3S$: % C, 53.41; % H, 8.56; % N, 5.66. Found: % C, 53.11; % H, 8.30; % N, 5.44. Ion Electrospray Mass Spectrum: M−1=246

Example 1
Preparation of N-[2-[4-hydroxy-4-(2-thienyl)cyclohexyl]propyl] 2-propanesulfonamide, cis- and trans- isomers.

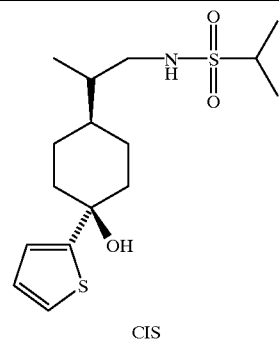

CIS

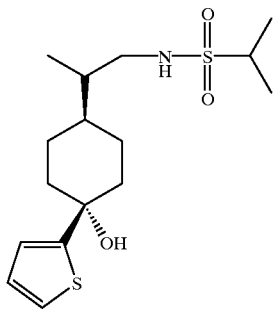

TRANS

To a solution of 0.3 g (1.14 mmol) of material from Preparation 2 in 4 ml of THF was added 2.85 ml of a 1M solution of 2-thienyllithium (2.85 mmol) at ambient temperature under nitrogen atmosphere. The mixture was stirred for 2 h. and quenched with $NH_4Cl$ saturated solution and extracted three times with diethyl ether. The organic phase was dried over $Na_2SO_4$, filtered and concentrated in vacuo. Chromatography (75 g of silica gel, 50% ethyl acetate/hexane) of the residue afforded 252 mg (64%) of the title compounds. Cis-Isomer: Analysis calculated for $C_{16}H_{27}NO_3S_2$: % C, 55.62; % H, 7.88; % N, 4.05. Found: % C, 55.88; % H, 7.87; % N, 4.27. Field Desorption Mass Spectrum: M=345. Trans-Isomer: Analysis calculated for $C_{16}H_{27}NO_3S_2$: % C, 55.62; % H, 7.88; % N, 4.05. Found: % C, 55.82; % H, 7.82; % N, 4.05. Ion Electrospray Mass Spectrum: M−18=327.

Example 2
Preparation of N-[2-[4-hydroxy-4-(3-thienyl)cyclohexyl]propyl] 2-propanesulfonamide, cis-isomer.

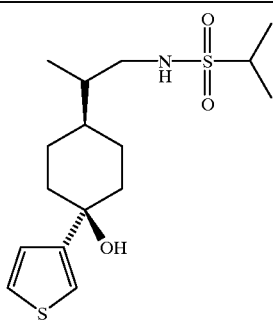

To a solution of 1.56 g (9.55 mmol) of 3-bromothiophene in 6 ml of diethyl ether was added 6 ml of a 1.6 M solution of butyllithium in hexane (9.55 mmol) at −78° C. under nitrogen atmosphere. The mixture was stirred for 30 min and then 1.0 g (3.82 mmol) of material from Preparation 2 was added at −78° C. The bath was removed and the mixture was stirred at ambient temperature overnight. The mixture was stirred for 2 h. and quenched with $NH_4Cl$ saturated solution and extracted three times with ethyl acetate. The organic phase was dried over $Na_2SO_4$, filtered and concentrated in vacuo. Chromatography (100 g of silica gel, 33% ethyl acetate/hexane) of the residue afforded 410 mg (30%) of the title compound. Cis-Isomer: Analysis calculated for $C_{16}H_{27}NO_3S_2$ $0.25H_2O$: % C, 54.90; % H, 7.92; % N, 4.00. Found: % C, 54.95; % H, 7.88; % N, 3.85. Ion Electrospray Mass Spectrum: M−1=344.

Example 3
Preparation of N-[2-[4-hydroxy-4-(5-(pyrid-2-yl)-2-thienyl)cyclohexyl]propyl] 2-propanesulfonamide, cis-isomer.

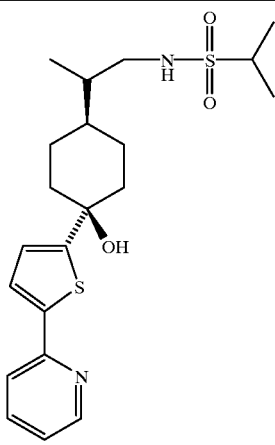

Prepared as in Example 2, using 1.0 g (3.82 mmol) of material from Preparation 2 and 2.23 g (9.56 mmol) of 2-bromo-5-(pyrid-2-yl)thiophene in 3 ml of THF and 6 ml of diethyl ether and 6 ml of a 1.6 M solution of butyllithium in hexane (9.55 mmol) at −20° C. Chromatography (150 g of silica gel, 50% ethyl acetate/hexane) of the residue afforded 420 mg (26%) of the title compound. Cis-Isomer: Analysis calculated for $C_{21}H_{30}N_2O_3S_2$ $1.25H_2O$: % C, 56.67; % H, 7.36; % N, 6.29. Found: % C, 56.95; % H, 7.12; % N, 5.89. Ion Electrospray Mass Spectrum: M+1=423.

Example 4
Preparation of N-[2-[4-hydroxy-4-(2-pyridyl)cyclohexyl]propyl] 2-propanesulfonamide, cis- and trans- isomers.

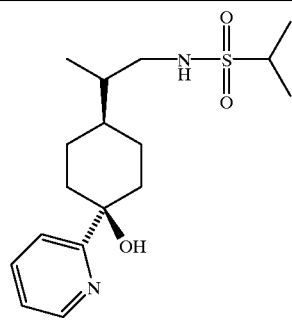

CIS

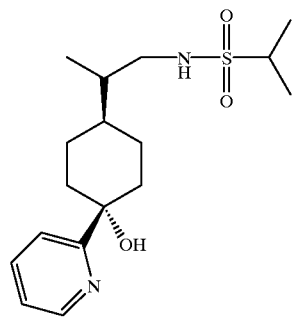

TRANS

Prepared as in Example 2, using 100 mg (0.38 mmol) of material from Preparation 2 and 150 mg (0.95 mmol) of 2-bromopyridine in 1.5 ml of THF and 0.59 ml of a 1.6 M solution of butyllithium in hexane (0.95 mmol) at −100° C. Chromatography (35 g of silica gel, 50% ethyl acetate/hexane) of the residue afforded 118 mg (90%) of the title compound. Cis-Isomer: Analysis calculated for $C_{17}H_{28}N_2O_3S$: % C, 59.97; % H, 8.29; % N, 8.23. Found: % C, 60.03; % H, 8.36; % N, 7.99. Field Desorption Mass Spectrum: M+1=341. Trans-Isomer: Analysis calculated for $C_{17}H_{28}N_2O_3S$: % C, 59.97; % H, 8.29; % N, 8.23. Found: % C, 59.85; % H, 8.39; % N, 7.94. Field Desorption Mass Spectrum: M=340.

Example 5
Preparation of N-[2-[4-hydroxy-4-phenyl-cyclohexyl]propyl] 2-propanesulfonamide, cis- and trans- isomers

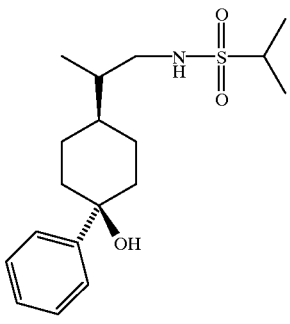

CIS

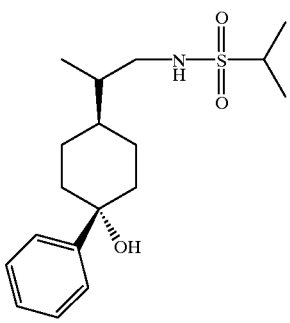

TRANS

Prepared as in Example 1, using 65 mg (0.25 mmol) of material from Preparation 2 and 0.2 ml of a 3 M solution of phenylmagnesium bromide in diethyl ether (0.62 mmol) at ambient temperature. Chromatography (20 g of silica gel, 50% ethyl acetate/hexane) of the residue afforded 60 mg (70%) of the title compound. Cis-Isomer: Analysis calculated for $C_{18}H_{29}NO_3S$ 0.25$H_2O$: % C, 62.85; % H, 8.64; % N, 4.07. Found: % C, 62.74; % H, 8.78; % N, 3.94. Field Desorption Mass Spectrum: M=339. Trans-Isomer: Field Desorption Mass Spectrum: M=339.

Example 6
Preparation of N-[2-[4-hydroxy-4-(2-thiazol)cyclohexyl]propyl] 2-propanesulfonamide (mixture of isomers).

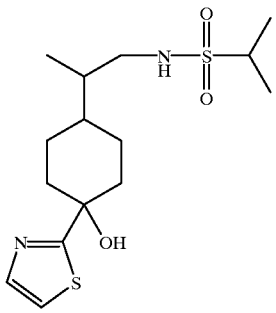

To a 1.95 ml of 1.6 M solution of butyllithium in hexane (2.85 mmol) in 4 ml of diethylether was added 467 mg (2.85 mmol) in 1 ml of diethylether at −78° C. under nitrogen atmosphere. The mixture was stirred for 20 min and then 300 mg (1.14 mmol) of material from Preparation 2 in 2 ml of THF was added at −78° C. The bath was removed and the mixture was stirred at ambient temperature overnight. The mixture was stirred for 1 h. and quenched with $NH_4Cl$ saturated solution and extracted three times with diethylether. The organic phase was dried over $Na_2SO_4$, filtered and concentrated in vacuo. Chromatography (50 g of silica gel, 50% ethyl acetate/hexane) of the residue afforded 255 mg (65%) of the title compound as a mixture of isomers. Analysis calculated for $C_{15}H_{26}N_2O_3S_2$ 0.9$H_2O$: % C, 49.67; % H, 7.73; % N, 7.72. Found: % C, 49.34; % H, 7.31; % N, 7.35. Field Desorption Mass Spectrum: M=346.

Example 7
Preparation of N-[2-[4-hydroxy-4-[4-(2,5-dimethyl-1H-pyrrol-1-yl)phenyl]cyclohexyl]propyl] 2-propanesulfonamide cis- and trans- isomers.

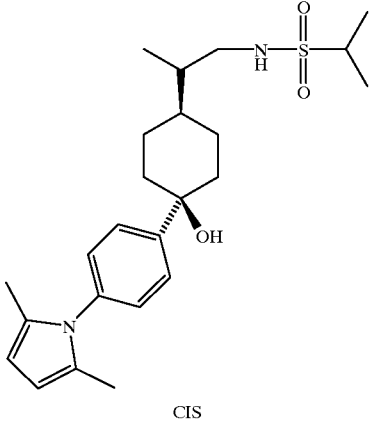

CIS

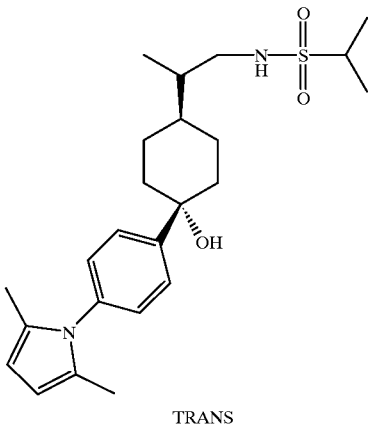

TRANS

Prepared as in Example 2, using 100 mg (0.38 mmol) of material from Preparation 2 237 mg (0.95 mmol) of 1-(4-bromophenyl)-2,5-dimethylpyrrole in 2 ml of diethyl ether and 0.6 ml of a 1.6 M solution of butyllithium in hexane (0.95 mmol) at −78° C. Chromatography (30 g of silica gel, 50% ethyl acetate/hexane) of the residue afforded 93 mg (56%) of the title compound. Cis-Isomer: Ion Electrospray Mass Spectrum: M+1=433. Trans-Isomer: Ion Electrospray Mass Spectrum: M+1=433.

Example 8
Preparation of N-[2-[4-(2-thienyl)-3-cyclohexen-1-yl]propyl] 2-propanesulfonamide.

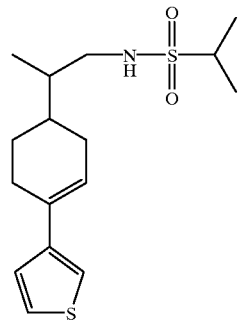

A solution of 80 mg (0.23 mmol) of the material prepared in Example 1 and 8 mg of p-toluenesulfonic acid in 2 ml of toluene, with 4A molecular sieves, was heated at 90° C. overnight. The mixture was filtered, and a saturated solution of NaHCO$_3$ was added, and extracted three times with diethyl ether. The organic phase was dried over Na$_2$SO$_4$, filtered and concentrated in vacuo. Chromatography (20 g of silica gel, 25% ethyl acetate/hexane) of the residue afforded 48 mg (75%) of the title compound. Analysis calculated for C$_{16}$H$_{25}$NO$_2$S$_2$ 0.05H$_2$O: % C, 58.52; % H, 7.70; % N, 4.26. Found: % C, 58.89; % H, 7.54; % N, 4.08. Field Desorption Mass Spectrum: M=327.

Example 9
Preparation of N-[2-[4-(3-thienyl)-3-cyclohexen-1-yl]propyl] 2-propanesulfonamide.

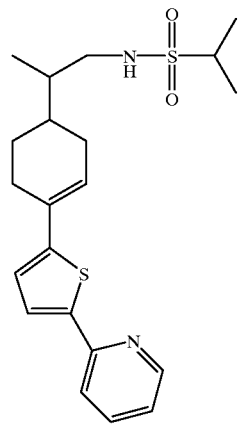

A solution of 40 mg (0.12 mmol) of the material prepared in Example 2 was dissolved in chloroform-d and evaporated and heated at 60° C. in vacuo overnight. Afforded 38 mg (97%) of the title compound. Analysis calculated for C$_{16}$H$_{25}$NO$_2$S$_2$ 0.33H$_2$O: % C, 57.63; % H, 7.76; % N, 4.20. Found: % C, 58.01; % H, 8.16; % N, 4.33. Ion Electrospray Mass Spectrum: M+1=328.

Example 10
Preparation of N-[2-[4-[5-(pyrid-2-yl)-2-thienyl]-3-cyclohexen-1-yl]propyl] 2-propanesulfonamide.

Prepared as in Example 9, using 18 mg (0.042 mmol) of the material prepared in Example 3. Afforded 16 mg (100%) of the title compound. Ion Electrospray Mass Spectrum: M+1=405.

Example 11
Preparation of N-[2-[4-(2-thiazol)-3-cyclohexen-1-yl]propyl] 2-propanesulfonamide.

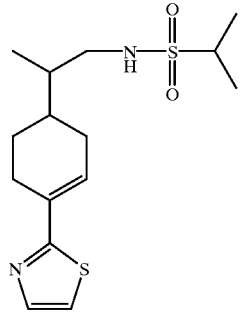

Prepared as in Example 8, using 100 mg (0.29 mmol) of the material prepared in Example 6 and 10 mg of p-toluenesulfonic acid. Afforded 32 mg (34%) of the title compound. Field Desorption Mass Spectrum: M=328.

Example 12
Preparation of N-[2-[4-(2-pyridyl)-3-cyclohexen-1-yl]propyl] 2-propanesulfonamide.

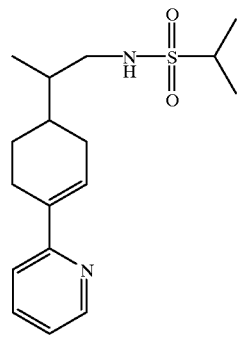

A solution of 50 mg (0.15 mmol) of the material prepared in Example 4 in 1 ml of toluene, and 89 mg (0.38 mmol) of (methoxycarbonylsulfamoyl)triethylammonium hydroxide, was heated at 60° C. for 4 h. The solution was concentrated in vacuo. Chromatography (25 g of silica gel, 25% ethyl acetate/hexane) of the residue afforded 29 mg (60%) of the title compound. Field Desorption Mass Spectrum: M=322.

Example 13
Preparation of N-[2-[4-[4-formylphenyl]-3-cyclohexen-1-yl]propyl] 2-propanesulfonamide.

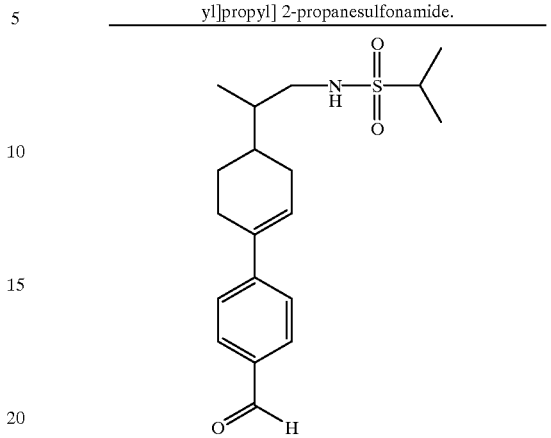

A. N-[2-[4-[[(trifluoromethyl)sulfonyl]oxy]-3-cyclohexen-1-yl]propyl] 2-propanesulfonamide: To a −78° C. solution of 1.0 g (3.82 mmol) of the material prepared in Preparation 2 in 6 ml of THF was added 8.4 ml of a 1 M solution of lithium bis(trimethylsilyl)amide in THF (8.4 mmol). The bath was removed and the mixture was stirred for 30 min and then 1.46 g (4.09 mmol) of N-phenyltrifluoromethane sulfonimide was added at ambient temperature. The mixture was stirred for 24 h. The reaction was quenched with $NH_4Cl$ saturated solution and extracted three times with ethyl acetate. The organic phase was dried over $Na_2SO_4$, filtered and concentrated in vacuo. Chromatography (125 g of silica gel, 15% ethyl acetate/hexane) of the residue afforded 395 mg (26%) of the title compound.

B. A solution of 50 mg (0.13 mmol) of the material prepared in step A, 21 mg (0.14 mmol) of 4-formylbenzeneboronic acid, 177 mg (0.78 mmol) of benzyltriethylammonium chloride, 34 mg (0.35 mmol) of sodium carbonate and 4 mg (0.006 mmol) of bis(triphenylphosphine)palladium chloride in 1 ml of dioxane was heated at 100° C. overnight. The mixture was filtered over celite, and water was added. The aqueous portion was extracted three times with ethyl acetate. The organic phase was dried over $Na_2SO_4$, filtered and concentrated in vacuo. Chromatography (20 g of silica gel, 20% ethyl acetate/hexane) of the residue afforded 15 mg (33%) of the title compound. Analysis calculated for $C_{19}H_{27}NO_3S$ $H_2O$: % C, 62.10; % H, 7.95; % N, 3.81. Found: % C, 62.22; % H, 8.62; % N, 4.00. Ion Electrospray Mass Spectrum: M−1=348.

Example 14
Preparation of N-[2-[4-(4-cyanophenyl)-3-cyclohexen-1-yl]propyl] 2-propanesulfonamide.

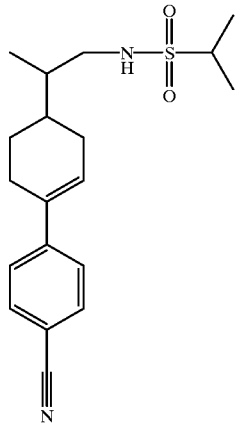

A solution of 350 mg (0.89 mmol) of the material prepared in step A of Example 13, 4.5 ml of a 0.05 M solution of iodo 4-(cyanophenyl)zinc (2.23 mmol) and 32 mg (0.045 mmol) of bis(triphenylphosphine)palladium chloride in 3 ml of THF was heated at 60° C. overnight. The mixture was cooled and diluted with water, the aqueous portion was extracted three times with ethyl acetate. The organic phase was dried over $Na_2SO_4$, filtered and concentrated in vacuo. Chromatography (75 g of silica gel, 15% ethyl acetate/hexane) of the residue afforded 195 mg (63%) of the title compound. Analysis calculated for $C_{19}H_{26}N_2O_2S$: % C, 65.85; % H, 7.56; % N, 8.09. Found: % C, 66.09; % H, 7.48; % N, 7.91. Field Desorption Mass Spectrum: M=346.

Example 15
Preparation of N-[2-[4-(4-cyanomethylphenyl)-3-cyclohexen-1-yl]propyl 2-propanesulfonamide.

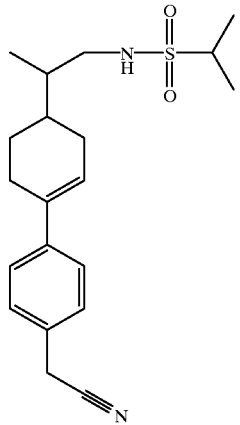

Prepared as in Example 14, using 370 mg (0.94 mmol) of the material prepared in step A of Example 13, 5.9 ml of a 0.4 M solution of iodo 4-(cyanomethylphenyl)zinc (2.35 mmol) and 33 mg (0.047 mmol) of bis(triphenylphosphine) palladium chloride in 3 ml of THF. Afforded 195 mg (57%) of the title compound. Analysis calculated for $C_{20}H_{28}N_2O_2S$ $0.4H_2O$: % C, 65.33; % H, 7.89; % N, 7.62. Found: % C, 65.04; % H, 7.87; % N, 7.31. Ion Electrospray Mass Spectrum: M−1=359.

Example 16
Preparation of N-[2-[4-(4-cyclopentyl)-3-cyclohexen-1-yl]propyl] 2-propanesulfonamide.

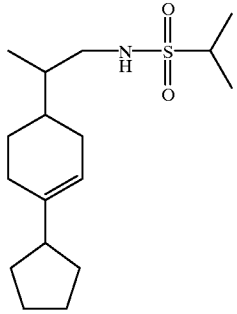

Prepared as in Example 14, using 100 mg (0.25 mmol) of the material prepared in step A of Example 13, 1.25 ml of a 0.5 M solution of bromo cyclopentylzinc (0.63 mmol) and 9 mg (0.012 mmol) of bis(triphenylphosphine)palladium chloride in 1 ml of THF. Afforded 35 mg (45%) of the title compound. Ion Electrospray Mass Spectrum: M+1=314.

Example 17
Preparation of N-[2-[4-[4-(aminomethyl)phenyl]-3-cyclohexen-1-yl]propyl] 2-propanesulfonamide.

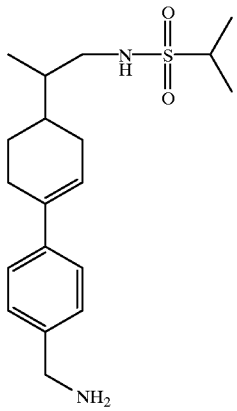

To a suspension of 33 mg (0.87 mmol) of lithium aluminum hydride in 0.5 ml of diethyl ether, 100 mg (0.29 mmol) of the material prepared in Example 14 in 0.5 ml of diethyl ether and 0.5 ml of THF. The mixture was stirred for 3 h. $Na_2SO_4$ $10H_2O$ was added, and the mixture stirred for 30 min at ambient temperature. The solid was filtered and the organic solution was concentrated in vacuo. Precipitation with diethyl ether afforded 65 mg (64%) of the title compound. Analysis calculated for $C_{19}H_{30}N_2O_2S$ $0.75H_2O$: % C, 62.69; % H, 8.72; % N, 7.69. Found: % C, 62.73; % H, 7.96; % N, 7.32. Field Desorption Mass Spectrum: M=350.

Example 18
Preparation of N-[2-[4-[4-(isopropylsulfonylaminomethyl)phenyl]-3-cyclohexen-1-yl]propyl] 2-propanesulfonamide.

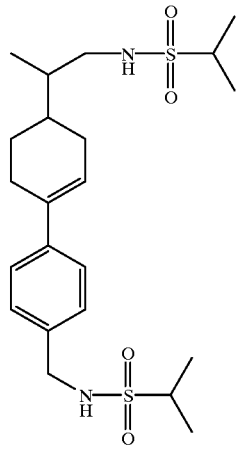

A solution of the material from Example 17, 50 mg, (0.14 mmol) in dichloromethane (1 ml) was cooled to 0° C., 1,8-diazabicyclo[5.4.0]undec-7-ene 26 mg (0.17 mmol) was added, followed by isopropylsulfonyl chloride (25 mg, 0.17 mmol). The ice-bath was removed and the solution was stirred at ambient temperature overnight. The organic solution was washed with 1 N hydrochloric acid, sodium bicarbonate saturated solution, brine, dried over $Na_2SO_4$ filtered and concentrated in vacuo. Chromatography (20 g of silica gel, 33% ethyl acetate/hexane) of the residue afforded 27 mg (42%) of the title compound. Analysis calculated for $C_{22}H_{36}N_2O_4S_2$ $0.25H_2O$: % C, 57.30; % H, 7.98; % N, 6.07. Found: % C, 57.49; % H, 8.01; % N, 5.68. Field Desorption Mass Spectrum: M+1=457.

Example 19
Preparation of N-[2-[4-(4-aminophenyl)3-cyclohexen-1-yl]propyl] 2-propanesulfonamide.

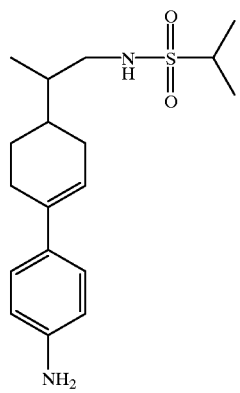

A solution of 25 mg (0.058 mmol) of the material prepared in Example 7 in 0.8 ml of ethanol and 0.2 ml of water, and 20 mg (0.29 mmol) of hydroxylamine hydrochloride, was heated at 60° C. overnight. The organic solution was washed with 1N hydrochloric acid. The aqueous portion was washed with diethyl ether, and 2 M NaOH solution. The basic aqueous portion was extracted three times with diethyl ether, dried over $Na_2SO_4$ filtered and concentrated in vacuo. Afforded 11 mg (50%) of the title compound. Ion Electrospray Mass Spectrum: M+1=337.

Example 20
Preparation of N-[2-[4-phenylcarboxamidocyclohexyl]propyl] 2-propanesulfonamide.

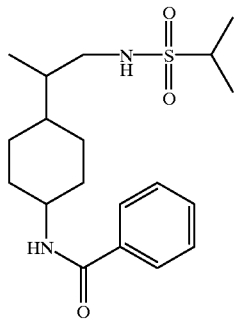

A. N-[2-[4-aminocyclohexyl]propyl] 2-propanesulfonamide: To a suspension of 17 mg (0.45 mmol) of lithium aluminum hydride in 1 ml of diethylether, 25 mg (0.09 mmol) of the material prepared in Preparation 4 in 0.5 ml of diethyl ether was added. The mixture was stirred overnight for 24 hrs. $Na_2SO_4.10H_2O$ was added, and the mixture stirred for 30 min at ambient temperature. The solid was filtered and the organic solution was concentrated in vacuo. Afforded 24 mg (100%) of the title compound.

B. N-[2-[4-phenylcarboxamidocyclohexyl]propyl]2-propanesulfonamide: A solution of the material from step A, 24 mg, (0.091 mmol) in dichloromethane (1 ml) was cooled to 0° C., triethylamine 11 mg (0.11 mmol) was added, followed by benzoyl chloride (15 mg, 0.11 mmol). The ice-bath was removed and the solution was stirred at ambient temperature overnight. The organic solution was washed with 1 N hydrochloric acid, sodium bicarbonate saturated solution, brine, dried over $Na_2SO_4$ filtered and concentrated in vacuo. Chromatography (10 g of silica gel, 50% ethyl acetate/hexane) of the residue afforded 18 mg (58%) of the title compound. Field Desorption Mass Spectrum: M=366.

Example 21
Preparation of N-[2-[4-(benzyloxyimino)cyclohexyl]propyl] 2-propanesulfonamide.

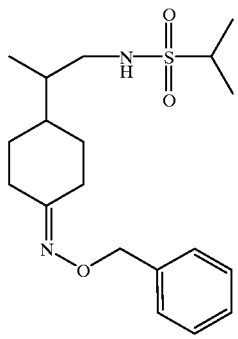

A solution of 100 mg (0.38 mmol) of the material prepared in Preparation 2 in 2 ml of dichloromethane, 60 mg (0.38 mmol) of benzyloxyamine hydrochloride and 60 mg (0.76 mmol) of pyridine was stirred for 4 hrs at 60° C. The organic solution was washed with 1 N hydrochloric acid, sodium bicarbonate saturated solution, brine, dried over $Na_2SO_4$ filtered and concentrated in vacuo. Chromatography (75 g of silica gel, 25% ethyl acetate/hexane) of the residue afforded 128 mg (92%) of the title compound. Analysis calculated for $C_{19}H_{30}N_2O_3S$: % C, 62.26; % H, 8.25; % N, 7.64. Found: % C, 62.67; % H, 8.06; % N, 6.99. Ion Electrospray Mass Spectrum: M+1=367.

Example 22
Preparation of N-[2-[4-(2-thienyl)cyclohexyl]propyl] 2-propanesulfonamide.

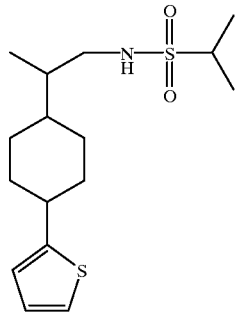

To a solution of 80 mg (0.23 mmol) of the material prepared in Example 1 in 2 ml of dichloromethane and 32 mg (0.28 mmol) of triethylsilane at −78° C., was added 49 mg (0.35 mmol) of boron trifluoride diethyl etherate. The mixture was stirred for 1 h., the bath was removed and stirred at ambient temperature for 30 min. A saturated solution of sodium bicarbonate (2 ml) was added and extracted with dichloromethane, dried over $Na_2SO_4$, filtered and concentrated in vacuo. Chromatography (75 g of silica gel, 25% ethyl acetate/hexane) of the residue afforded 38 mg (50%) of the title compound. Analysis calculated for $C_{16}H_{27}NO_2S_2$: % C, 58.32; % H, 8.26; % N, 4.25. Found: % C, 59.06; % H, 8.48; % N, 4.31. Field Desorption Mass Spectrum: M=329.

Example 23
Preparation of N-[2-[spiro[isobenzofuran-1(3H)-4'-cyclohexyl]propyl] 2-propanesulfonamide.

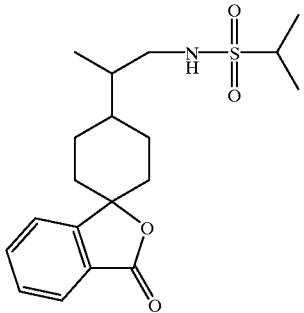

To a −78° C. solution of 168 mg (0.95 mmol) of N,N-diethylbenzamide, 44 mg (0.38 mmol) of N,N,N',N'-tetramethyl ethylenediamine in 2 ml of THF, was added 0.73 ml ml of a 1.3 M solution of sec-butyllithium (0.95 mmol). After stirring for 1 h, 100 mg (0.38 mmol) of the material prepared in Preparation 2 in 0.5 ml of THF was added at −78° C. The bath was removed and the reaction mixture was stirred at ambient temperature overnight. The reaction was quenched with $NH_4Cl$ saturated solution and extracted three times with ethyl acetate. The organic phase was dried over $Na_2SO_4$, filtered and concentrated in vacuo. Chromatography (75 g of silica gel, 33% ethyl acetate/hexane) of the residue afforded 11 mg (8%) of the title compound and 98 mg (59%) of a diastereomeric mixture of N-[2-[4-hydroxy-4-(2-(N,N-diethylaminocarbonyl)phenyl)-cyclohexyl]propyl]-2-propanesulfonamide. Analysis calculated for $C_{19}H_{27}NO_4S$ $0.25H_2O$: % C, 61.68; % H, 7.49; % N, 3.79. Found: % C, 61.89; % H, 8.05; % N, 3.74. Field Desorption Mass Spectrum: M+1=366.

Example 24
Preparation of N-[2-[4-hydroxy-4-(2-thienyl)cyclohexyl]ethyl] 2-propanesulfonamide cis- and trans- isomers.

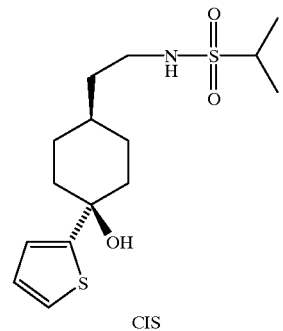

CIS

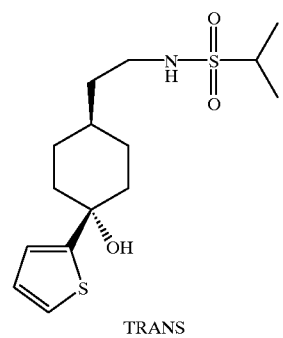

TRANS

To a solution of 250 mg (1.01 mmol) of material from Preparation 6 in 4 ml of THF was added 2.53 ml of a 1 M solution of 2-thienyllithium (2.53 mmol) at ambient temperature under nitrogen atmosphere. The mixture was stirred overnight, and quenched with $NH_4Cl$ saturated solution and extracted three times with diethyl ether. The organic phase was dried over $Na_2SO_4$, filtered and concentrated in vacuo. Chromatography (75 g of silica gel, 33% ethyl acetate/hexane) of the residue afforded 211 mg (63%) of the title compound. Cis-Isomer: Analysis calculated $C_{15}H_{25}NO_3S_2$: % C, 54.35; % H, 7.60; % N, 4.22. Found: % C, 54.65; % H, 7.37; % N, 4.40. Ion Electrospray Mass Spectrum: M+18=349. Trans-Isomer: Analysis calculated for $C_{15}H_{25}NO_3S_2$: % C, 54.35; % H, 7.60; % N, 4.22. Found: % C, 55.28; % H, 7.58; % N, 3.87. Ion Electrospray Mass Spectrum: M+18=349.

Example 25
Preparation of N-[2-[4-(2-thienyl)-3-cyclohexen-1-yl]propyl] 2-propanesulfonamide.

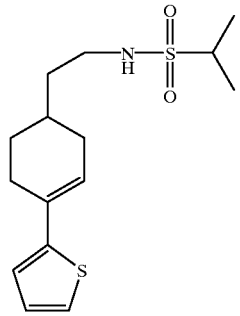

A solution of 20 mg (0.06 mmol) of the material prepared in Example 24 was dissolved in chloroform-d and evaporated and heated at 60° C. in vacuo for 3 days. Afforded 18 mg (97%) of the title compound. Analysis calculated for $C_{15}H_{23}NO_2S_2$: % C, 57.47; % H, 7.40; % N, 4.47. Found: % C, 57.49; % H, 7.51; % N, 4.45. Ion Electrospray Mass Spectrum: M+1=314.

Example 26
Preparation of N-[2-methyl-2-[4-hydroxy-4-(2-thienyl)-cyclohexyl]propyl] 2-propanesulfonamide cis-isomer.

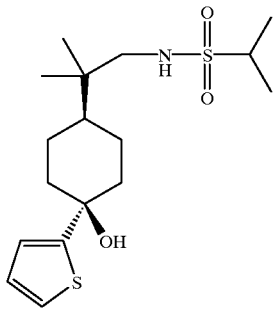

Prepared as in Example 1 using 3 g (11.47 mmol) of the material from Preparation 2, which contains 25% of N-[2-methyl-2-[4-oxocyclohexyl]propyl] 2-propanesulfonamide. Afforded 55 mg (6%) of the title compound. Cis-Isomer: Analysis calculated $C_{17}H_{29}NO_3S_2$: % C, 56.79; % H, 8.13; % N, 3.90. Found: % C, 56.25; % H, 7.81; % N, 4.30. Ion Electrospray Mass Spectrum: M-18=342.

Example 27
Preparation of N-[2-[4-hydroxy-4-(3-furyl)cyclohexyl]propyl] 2-propanesulfonamide, cis-isomer.

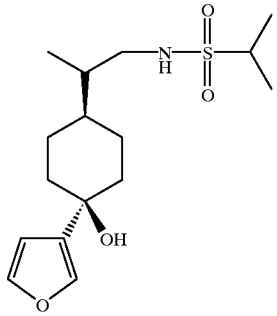

Prepared as in Example 2, using 0.5 g (1.91 mmol) of material from Preparation 2 and 0.7 g (4.77 mmol) of 3-bromofuran in 3 ml of THF and 3 ml of a 1.6 M solution of butyllithium in hexane (4.77 mmol) at −78° C. under nitrogen atmosphere. Chromatography (75 g of silica gel, 50% ethyl acetate/hexane) of the residue afforded 273 mg (44%) of the title compound. Ion Electrospray Mass Spectrum: M−1=328.

Example 28
Preparation of N- [2- [4- (4-methanesulfonylaminoethylphenyl) -3-cyclohexan-1-yl]propyl 2-propanesulfonamide (mixture of cis and trans isomers).

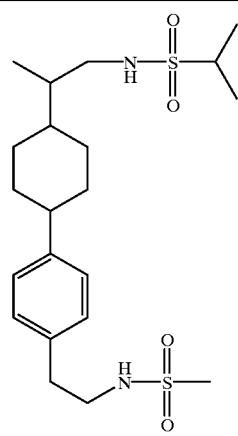

A. Preparation of N-[2-[4-(4-aminoethylphenyl)-3-cyclohexan-1-yl]propyl 2-propanesulfonamide; To a refluxing solution of 140 mg (0.39 mmol) of N-[2-[4-(4-cyanomethylphenyl)-3-cyclohexen-1-yl]propyl 2-propanesulfonamide (see Example 15) in 1 mL of tetrahydrofuran was added 0.043 mL (0.43 mmol) of borane dimethylsulfide complex via syringe. The mixture was refluxed for 60 min. then cooled to room temperature. To the solution was added 0.2 mL of 6 N hydrochloric acid and refluxing was continued for 60 min. The mixture was cooled and adjusted to pH 10 with 5 N aqueous sodium hydroxide. The mixture was diluted with 1 mL of water and extracted three times with 2 mL each of dichloromethane. The combined organic extracts were dried over $Na_2SO_4$, filtered and concentrated in vacuo to afford 78 mg (55%) of the title compound.

B. Preparation of final title compound; To a 0° C. solution of 78 mg (0.21 mmol) of material from step A and 23 mg (0.23 mmol) of triethylamine in 1 mL of dichloromethane was added 26 mg (0.23 mmol) of methanesulfonyl chloride. The ice bath was removed and the solution stirred for 2 h. To the mixture was added 2 mL of dichloromethane and 2 mL of 10% aqueous sodium bisulfate. The organic portion was separated and the aqueous portion was extracted three times with 2 mL each of dichloromethane. The combined organic extracts were dried over $Na_2SO_4$, filtered and concentrated in vacuo. Chromatography (2 g silica gel, 40% ethyl acetate/hexane) afforded 5 mg (5%) of the title compound.

Electrospray Mass Spectrum: M−1=443.

Example 28a
Preparation of N- [2- [4- (4-methanesulfonylaminoethylphenyl)-3-cyclohexan-1-yl]propyl 2-propanesulfonamide (Cis isomer).

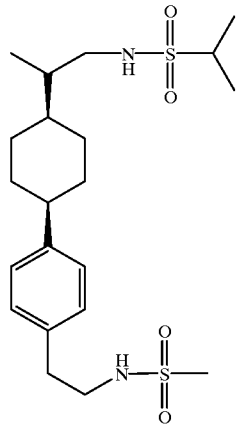

The title compound can be obtained by separating the mixture of cis and trans isomers prepared in example 28 by high performance liquid chromatography on a silica gel or alumina column with ethyl acetate/hexane, ethyl acetate/toluene or methanol/dichloromethane as the eluent under standard conditions.

Example 28b
Preparation of N- [2- [4- (4-methanesulfonylaminoethylphenyl)-3-cyclohexan-1-yl]propyl 2-propanesulfonamide (Trans isomer).

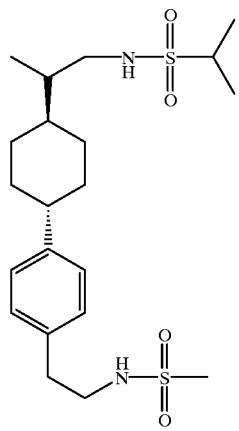

The title compound can be obtained by separating the mixture of cis and trans isomers prepared in example 28 by high performance liquid chromatography on a silica gel or alumina column with ethyl acetate/hexane, ethyl acetate/toluene or methanol/dichloromethane as the eluent under standard conditions.

Example 29
Preparation of N- [2- [4-(2-thienyl)-3-hydroxy-cyclohexyl]propyl] 2-propanesulfonamide.

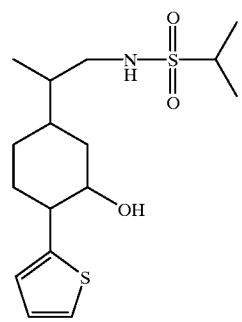

To a 0° C. solution of 1 eg. of N-[2-[4-(2-thienyl)-3-cyclohexen-1-yl]propyl] 2-propanesulfonamide (see example 8) in tetrahydrofuran is added 0.67 eq. of borane dimethyl sulfide complex. The mixture is stirred at 0° C. for 4 hr and slowly quenched with ethanol. To the 0° C. solution is added 3N aqueous sodium hydroxide then 30% aqueous hydrogen peroxide. The mixture is stirred at 0° C. for one hr. The organic portion is separated and the aqueous portion is extracted two times with diethyl ether. The combined organic extracts are dried over MgSO$_4$, filtered and concentrate in vacuo to provide the crude material. Chromatography (silica gel) of the crude material affords the purified title compound.

Example 30
Preparation of N- [2- [4-cyano-cyclohexyl]propyl] 2-propanesulfonamide.

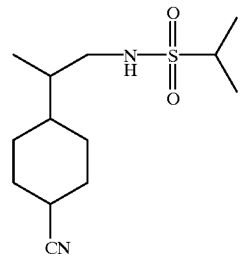

To a −15° C. solution of 1 eq. of N-[2-[4-oxocyclohexyl]propyl] 2-propanesulfonamide(see Preparation 2) and 1 eq. of tosylmethyl isocyanide in dimethoxyethane is added a solution of 2.8 eq. of potassium t-butoxide in t-butanol. The cooling bath is removed and the mixture is stirred for three hours. The mixture is then diluted with water and extracted three times with diethyl ether. The combined organic extracts are dried over MgSO$_4$, filtered and concentrated in vacuo to provide the crude material. Chromatography (silica gel) of the crude material affords the purified title compound.

Example 31

Preparation of N- [2- [4- (4-carboxymethylphenyl)-3-cyclohexen-1-yl]propyl 2-propanesulfonamide.

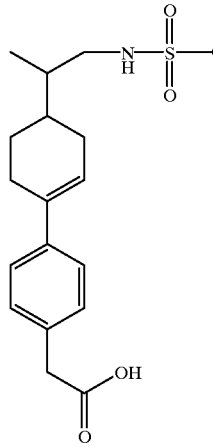

To a solution of N-[2-[4-(4-cyanomethylphenyl)-3-cyclohexen-1-yl]propyl 2-propanesulfonamide (see Example 15) in dioxane is added 5 N sodium hydroxide. The mixture is heated to 100° C. for 24 hr. The mixture is then cooled, and acidified with 10% aqueous sodium bisulfate. The mixture is extracted three times with ethyl acetate and the combined organic extracts are dried, filtered and concentrated in vacuo to afford the title compound.

Example 32

Preparation of N- [2- [4- (4-ethylcarboxymethylphenyl)-3-cyclohexen-1-yl]propyl 2-propanesulfonamide.

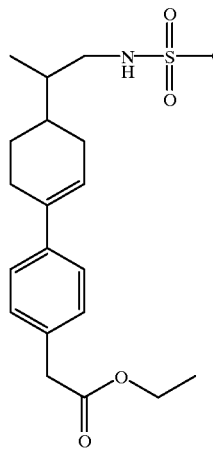

To a solution of N-[2-[4-(4-carboxymethylphenyl)-3-cyclohexen-1-yl]propyl 2-propanesulfonamide (see Example 31) in ethanol, bubble through hydrogen chloride gas until the mixture is saturated. Heat to 60° C. for 24 hr and then cool to room temperature and concentrate in vacuo. Add ethanol and concentrate in vacuo to afford the title compound.

Example 33

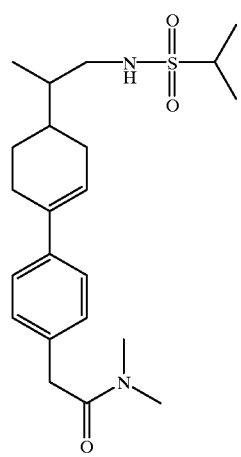

A solution of 1 equivalent of N-[2-[4-(4-carboxymethylphenyl)-3-cyclohexen-1-yl]propyl 2-propanesulfonamide (see Example 31) in tetrahydrofuran is treated with 10 eq. of thionyl chloride and stirred at room temperature for 16 hours. The mixture is then concentrate in vacuo, dissolved in dichloromethane and added to a 0° C. solution of 1 eq. of dimethylamine in dichloromethane. The mixture is stirred at 0° C. for 2 hours. and 10% aqueous sodium bisulfate is added. The organic layer is separated and the aqueous layer is extracted two times with dichloromethane. The combined organic extracts are dried over $NaSO_4$, filtered and concentrate in vacuo to provide the crude material. Chromatography of the crude material affords the title compound.

Example 34

Preparation of N- [2- [4- (4-carbomethoxythiazolin-2-yl)-cyclohex-1-yl]propyl] 2-propanesulfonamide.

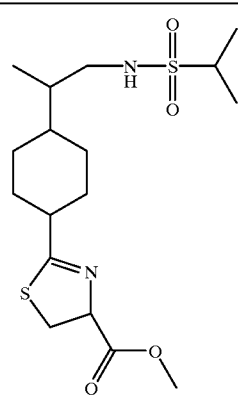

To a 0° C. solution of 1 eq. N-[2-[4-cyanocyclohexyl] propyl] 2-propanesulfonamide (see Example 30) in dichloromethane is added 1.1 eq. of 1,8-diazabicyclo[5.4.0]undec-7-ene. To the mixture is slowly added 1.05 eq. of bromotrichloromethane. The mixture is then stirred at 0° C. for two hours and saturated aqueous ammonium chloride is added. The organic portion is separated and the aqueous portion is extracted two times with dichloromethane. The combined organic extracts are dried over $NaSO_4$, filtered and concentrated in vacuo. Chromatography of the residue affords title compound.

Example 35
Preparation of N- [2- [4- (trimethyltin-cyclohexyl]propyl] 2-propanesulfonamide.

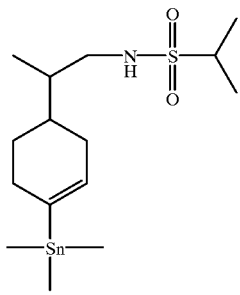

A mixture of 1 eq. of N-[2-[4-[[(trifluoromethyl)sulfonyl]oxy]-3-cyclohexen-1-yl]propyl] 2-propanesulfonamide (prepared in as shown in Example 13 Part A), 1.1 eq. of hexamethylditin, 3 eq. of lithium chloride, 0.1 eq of triphenylphosphine and 0.05 eq. of palladium acetate in tetrahydrofuran is heated to reflux for 24 hr. The mixture is cooled to room temperature, diluted with diethyl ether, filtered through celite and concentrated in vacuo to provide the crude material. Chromatography of the crude material affords purified title compound.

The following Table I provides additional compounds according to the present invention. The compounds can be prepared by one of ordinary skill in the art utilizing the techniques and procedures described hereinabove. The starting materials and reagents are available to one of ordinary skill in the art.

TABLE I

| Example | Compound |
|---------|----------|
| 36 | |
| 37 | |
| 38 | |
| 39 | |
| 40 | |
| 41 | |
| 42 | |

TABLE I-continued

| Example | Compound |
|---------|----------|
| 43 | *(structure)* |
| 44 | *(structure)* |
| 45 | *(structure)* |
| 46 | *(structure)* |
| 47 | *(structure)* |
| 48 | *(structure)* |
| 49 | *(structure)* |
| 50 | *(structure)* |
| 51 | *(structure)* |

TABLE I-continued
| Example | Compound |
|---|---|
| 52 | 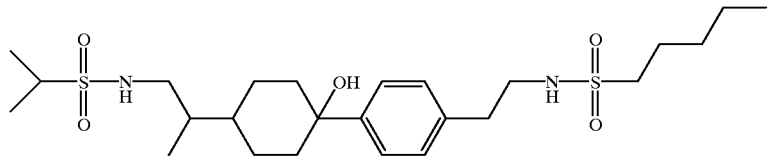 |
| 53 | 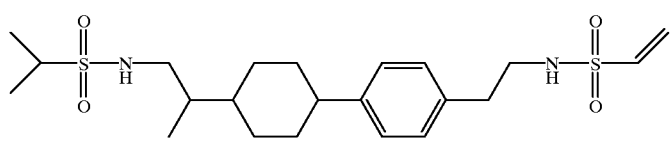 |
| 54 | 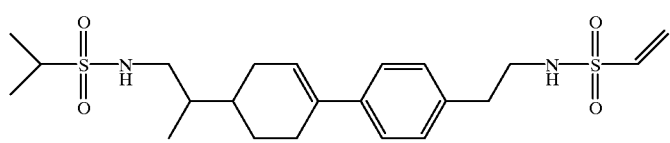 |
| 55 | 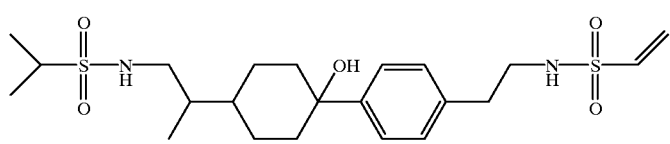 |
| 56 | 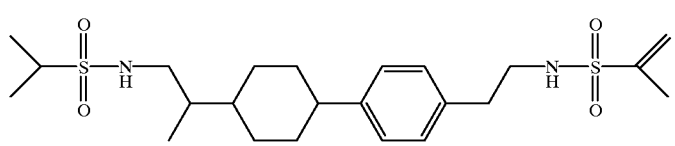 |
| 57 | 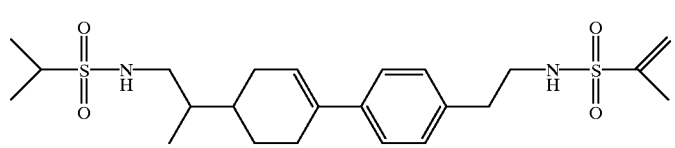 |
| 58 | 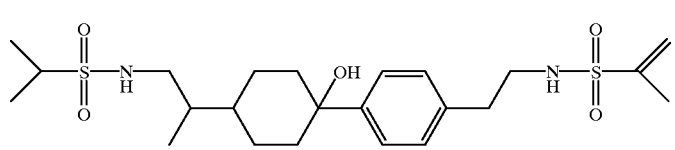 |
| 59 | 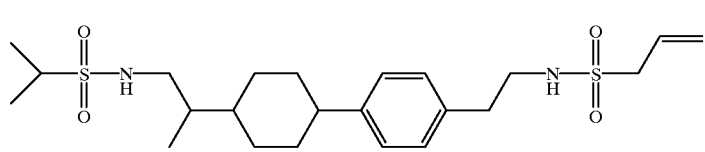 |
| 60 | 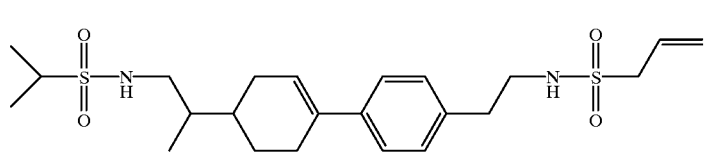 |
| 61 | 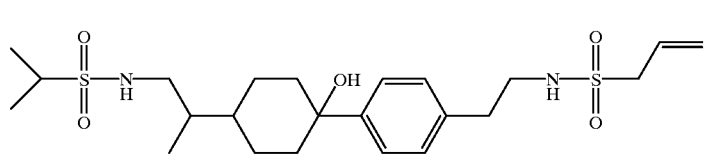 |

TABLE I-continued
| Example | Compound |
|---|---|
| 62 | 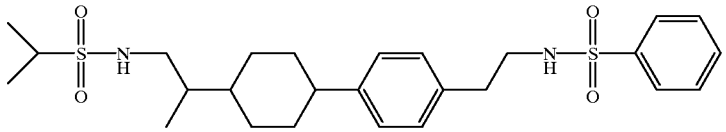 |
| 63 | 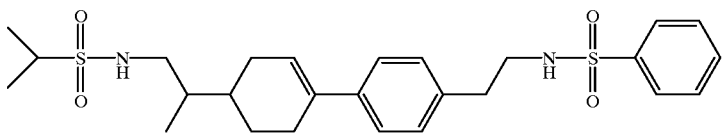 |
| 64 | 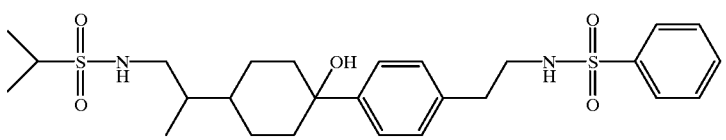 |
| 65 | 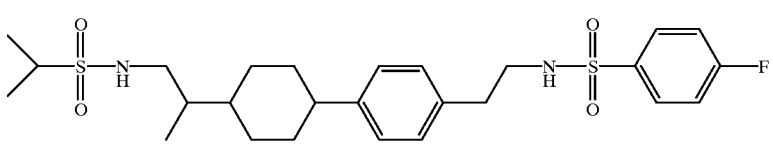 |
| 66 | 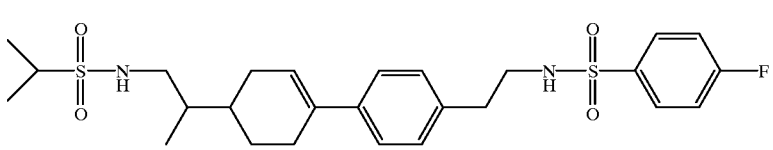 |
| 67 | 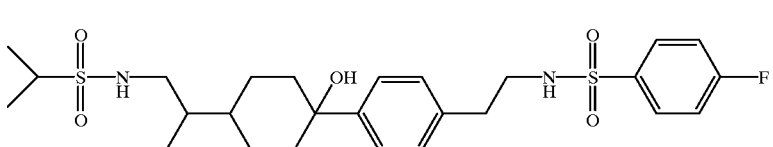 |
| 68 | 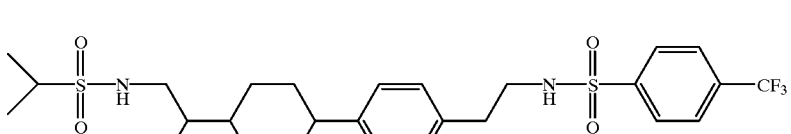 |
| 69 | 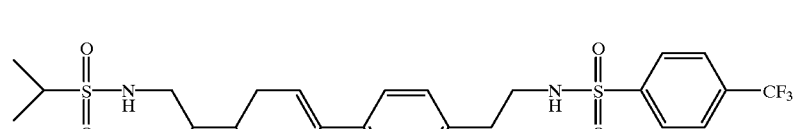 |
| 70 | 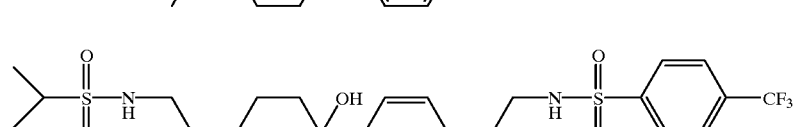 |
| 71 | 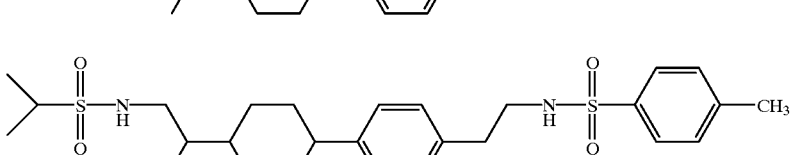 |

TABLE I-continued
| Example | Compound |
|---|---|
| 72 | 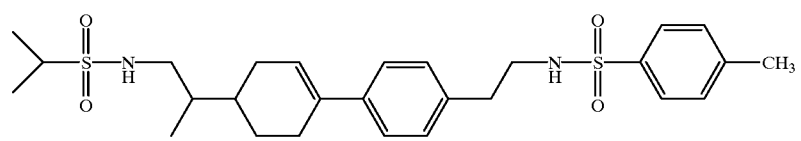 |
| 73 | 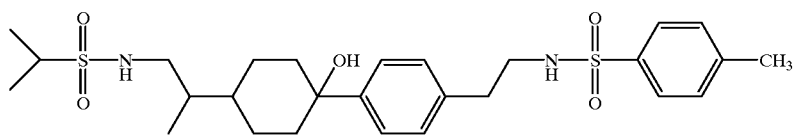 |
| 74 | 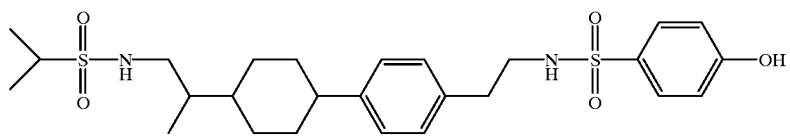 |
| 75 | 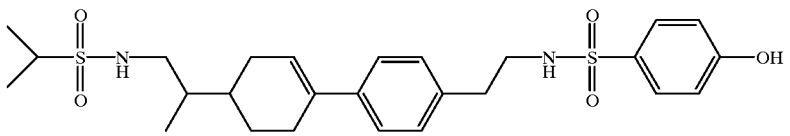 |
| 76 | 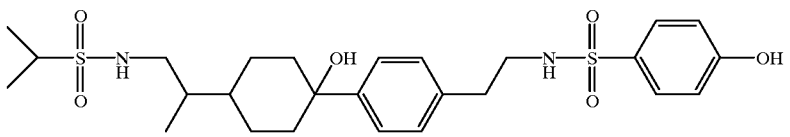 |
| 77 | 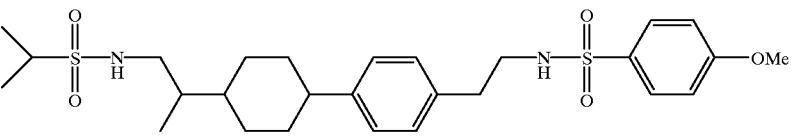 |
| 78 | 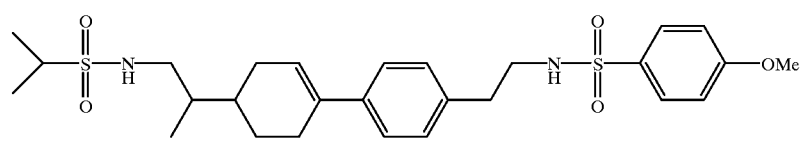 |
| 79 | 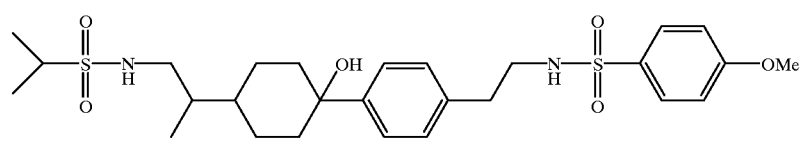 |
| 80 | 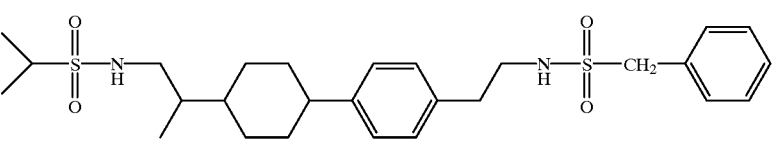 |
| 81 | 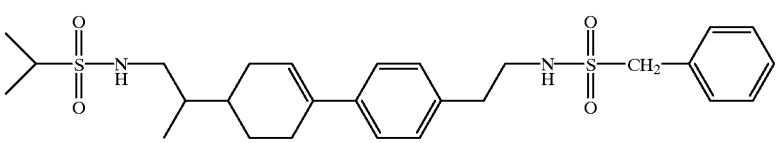 |

TABLE I-continued
| Example | Compound |
|---|---|
| 82 | 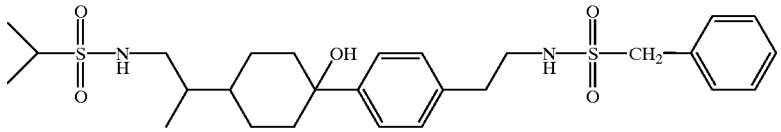 |
| 83 | 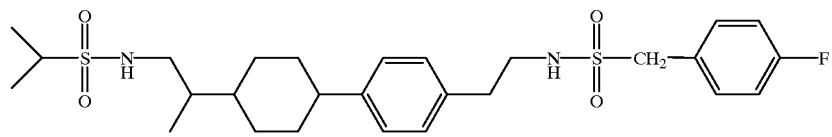 |
| 84 | 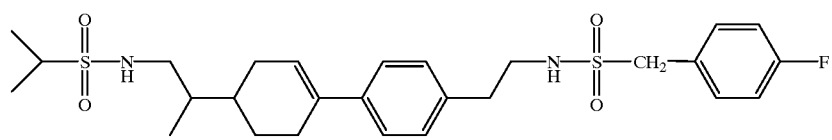 |
| 85 | 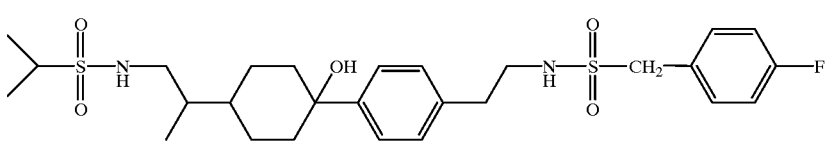 |
| 86 | 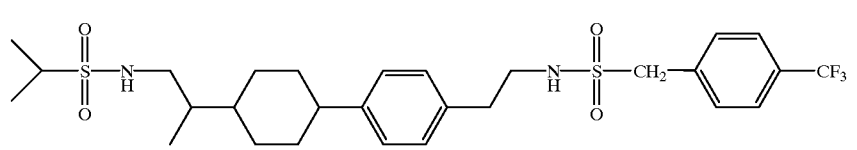 |
| 87 | 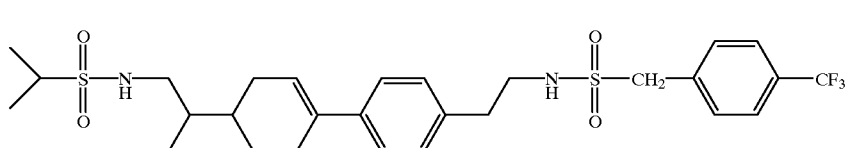 |
| 88 | 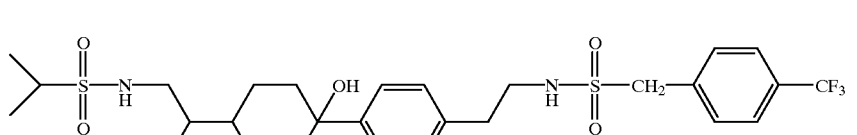 |
| 89 |  |
| 90 |  |
| 91 | 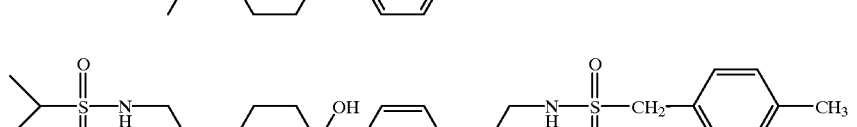 |

TABLE I-continued
| Example | Compound |
|---|---|
| 92 | 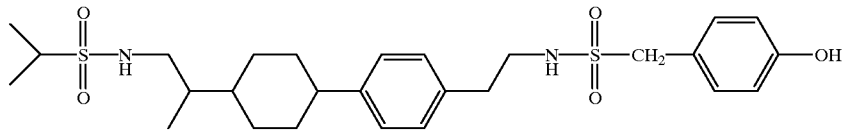 |
| 93 | 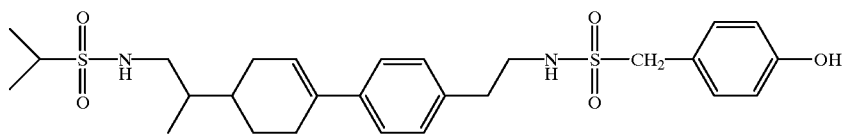 |
| 94 | 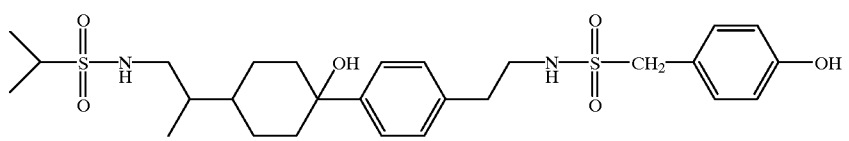 |
| 95 | 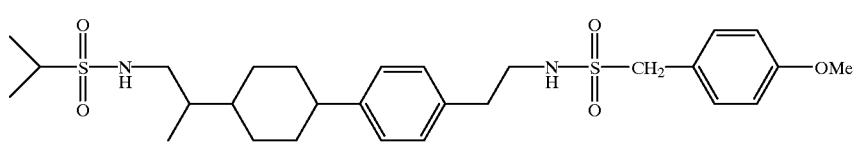 |
| 96 | 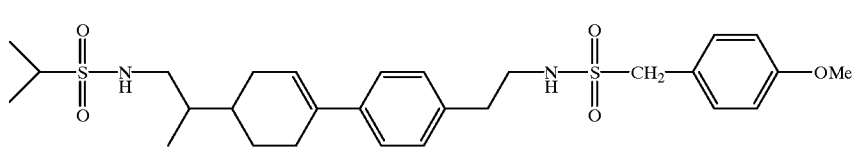 |
| 97 | 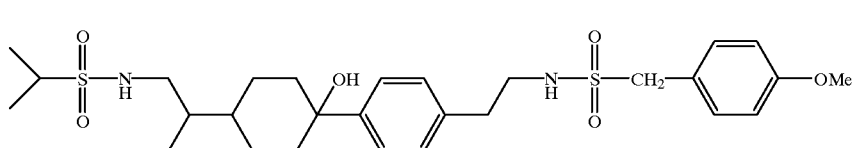 |
| 98 | 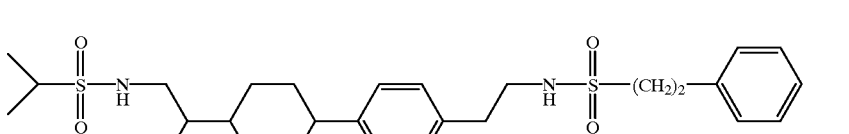 |
| 99 | 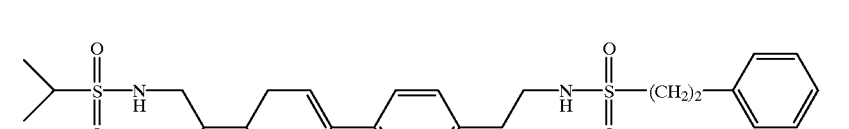 |
| 100 | 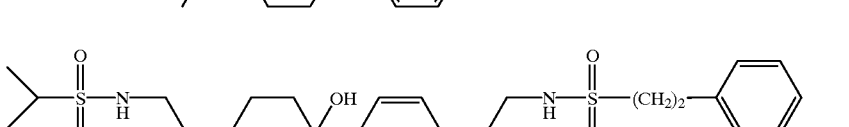 |
| 101 | 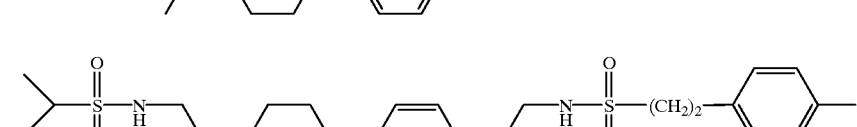 |

TABLE I-continued

| Example | Compound |
|---|---|
| 102 | (isopropyl)S(O)₂NH-CH₂-CH(CH₃)-[cyclohexenyl]-C₆H₄-CH₂CH₂-NHS(O)₂-(CH₂)₂-C₆H₄-F |
| 103 | (isopropyl)S(O)₂NH-CH₂-CH(CH₃)-[cyclohexyl(OH)]-C₆H₄-CH₂CH₂-NHS(O)₂-(CH₂)₂-C₆H₄-F |
| 104 | (isopropyl)S(O)₂NH-CH₂-CH(CH₃)-[cyclohexyl]-C₆H₄-CH₂CH₂-NHS(O)₂-(CH₂)₂-C₆H₄-CF₃ |
| 105 | (isopropyl)S(O)₂NH-CH₂-CH(CH₃)-[cyclohexenyl]-C₆H₄-CH₂CH₂-NHS(O)₂-(CH₂)₂-C₆H₄-CF₃ |
| 106 | (isopropyl)S(O)₂NH-CH₂-CH(CH₃)-[cyclohexyl(OH)]-C₆H₄-CH₂CH₂-NHS(O)₂-(CH₂)₂-C₆H₄-CF₃ |
| 107 | (isopropyl)S(O)₂NH-CH₂-CH(CH₃)-[cyclohexyl]-C₆H₄-CH₂CH₂-NHS(O)₂-(CH₂)₂-C₆H₄-CH₃ |
| 108 | (isopropyl)S(O)₂NH-CH₂-CH(CH₃)-[cyclohexenyl]-C₆H₄-CH₂CH₂-NHS(O)₂-(CH₂)₂-C₆H₄-CH₃ |
| 109 | (isopropyl)S(O)₂NH-CH₂-CH(CH₃)-[cyclohexyl(OH)]-C₆H₄-CH₂CH₂-NHS(O)₂-(CH₂)₂-C₆H₄-CH₃ |
| 110 | (isopropyl)S(O)₂NH-CH₂-CH(CH₃)-[cyclohexyl]-C₆H₄-CH₂CH₂-NHS(O)₂-(CH₂)₂-C₆H₄-OH |
| 111 | (isopropyl)S(O)₂NH-CH₂-CH(CH₃)-[cyclohexenyl]-C₆H₄-CH₂CH₂-NHS(O)₂-(CH₂)₂-C₆H₄-OH |

TABLE I-continued
| Example | Compound |
|---|---|
| 112 | 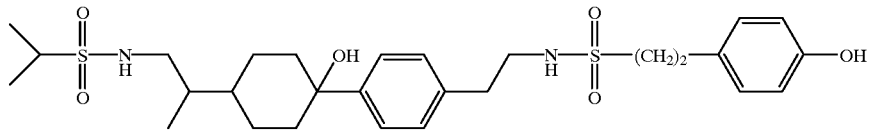 |
| 113 | 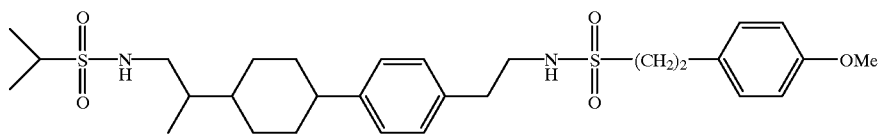 |
| 114 | 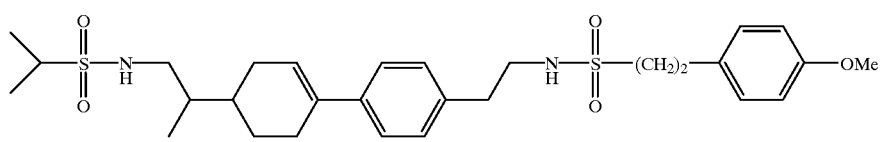 |
| 115 | 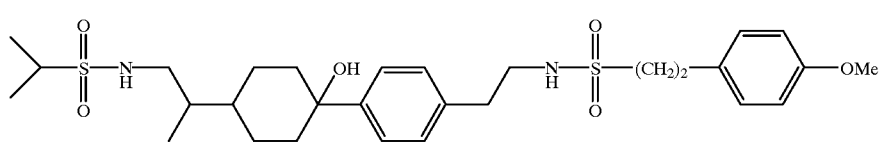 |
| 116 | 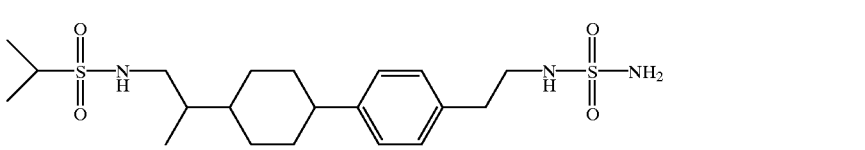 |
| 117 | 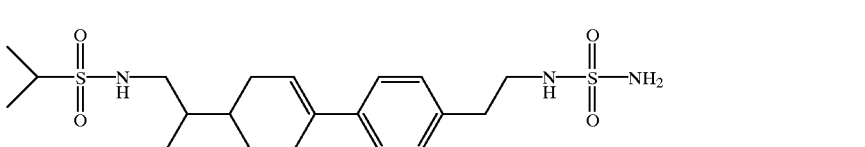 |
| 118 | 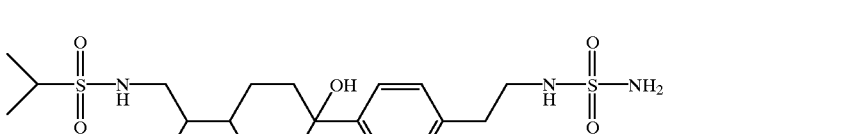 |
| 119 | 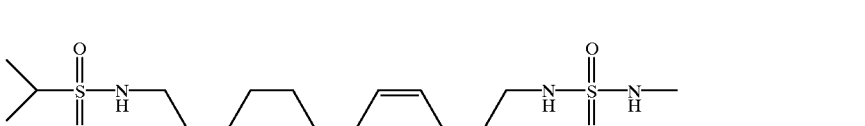 |
| 120 | 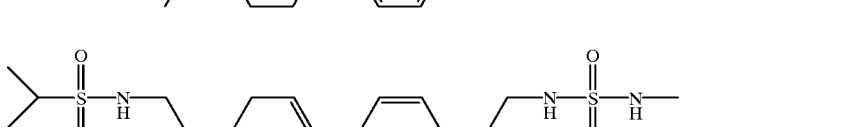 |
| 121 | 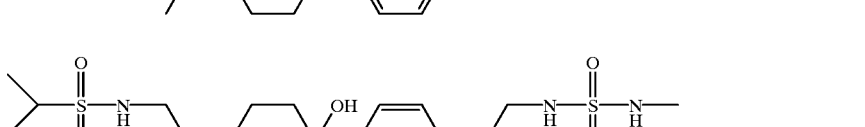 |

TABLE I-continued
| Example | Compound |
|---|---|
| 122 | 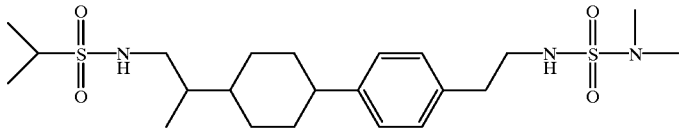 |
| 123 | 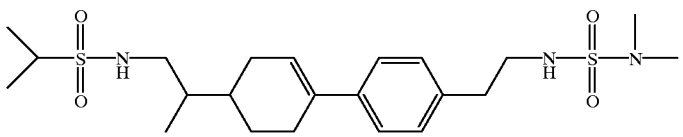 |
| 124 | 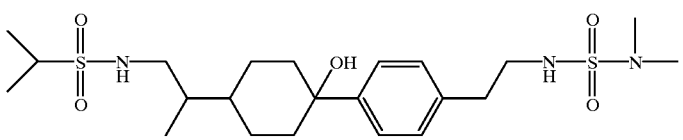 |
| 125 | 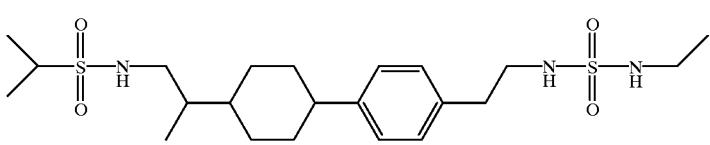 |
| 126 | 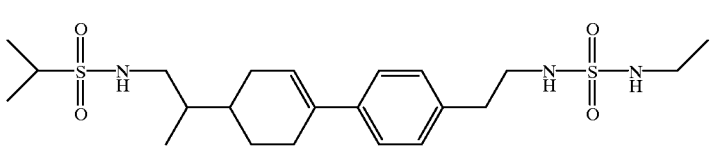 |
| 127 | 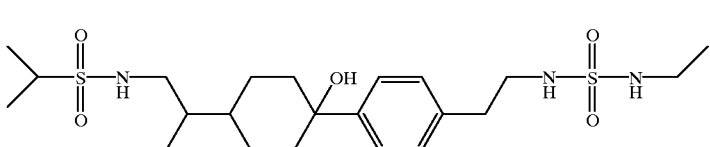 |
| 128 | 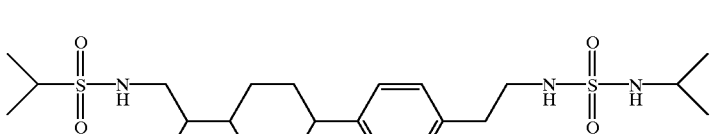 |
| 129 | 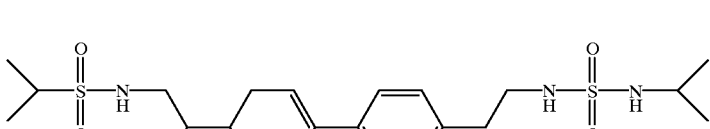 |
| 130 | 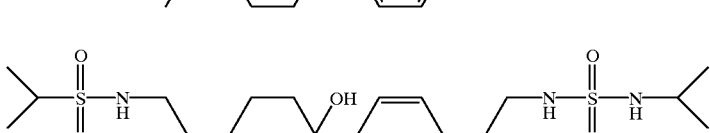 |
| 131 | 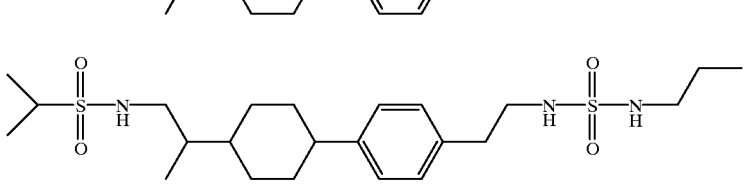 |

TABLE I-continued

| Example | Compound |
|---|---|
| 132 | |
| 133 | |
| 134 | |
| 135 | |
| 136 | |
| 137 | |
| 138 | |
| 139 | |
| 140 | |

TABLE I-continued
| Example | Compound |
|---|---|
| 141 | 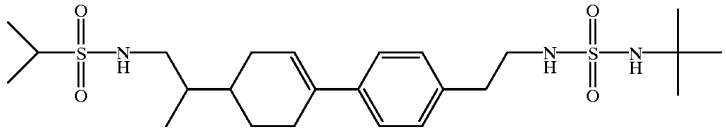 |
| 142 | 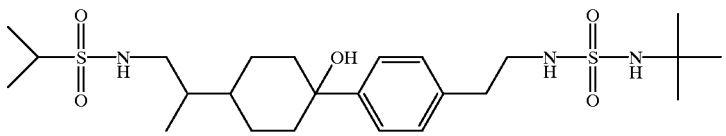 |
| 143 | 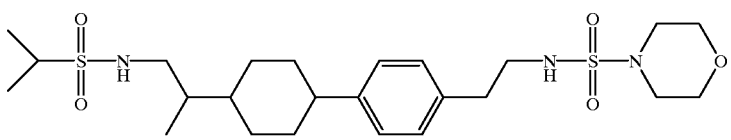 |
| 144 | 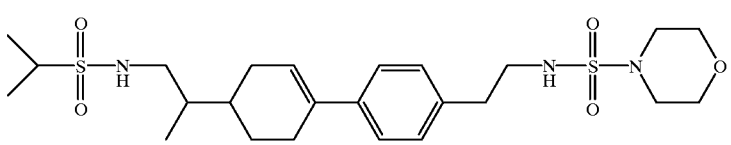 |
| 145 | 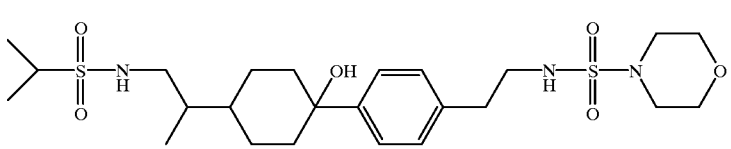 |
| 146 | 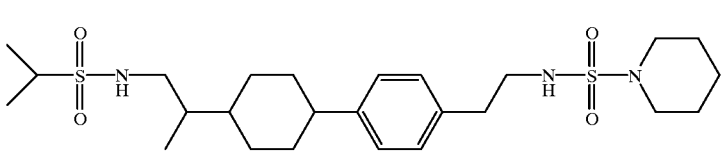 |
| 147 | 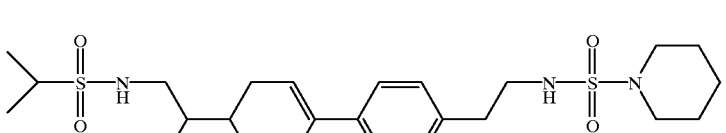 |
| 148 | 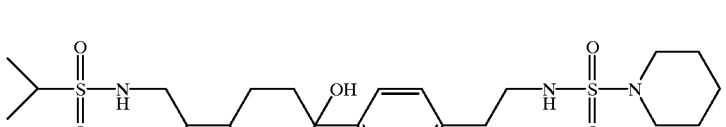 |
| 149 | 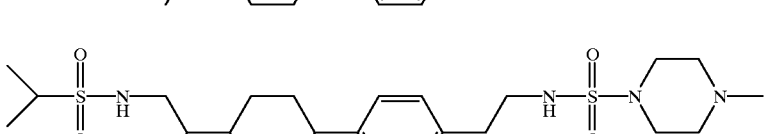 |
| 150 | 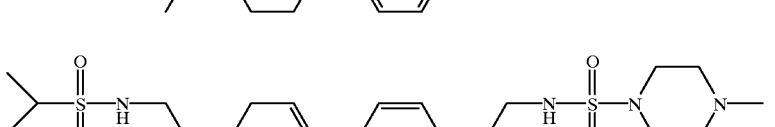 |

TABLE I-continued

| Example | Compound |
|---------|----------|
| 151 | 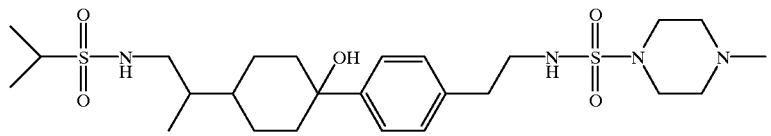 |
| 152 | 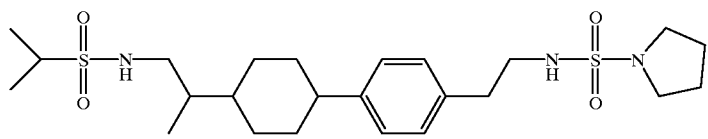 |
| 153 | 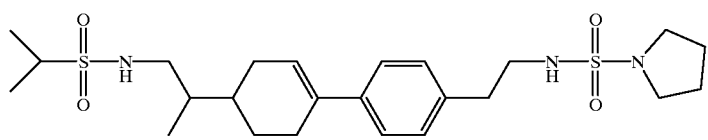 |
| 154 | 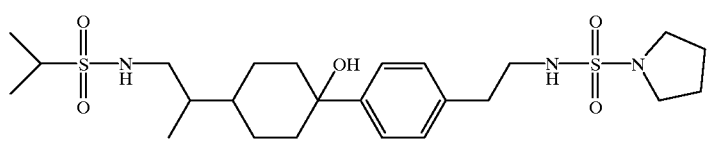 |

Further included within the scope of the present invention are the individual cis and trans isomers of the above examples. For example, the following individual cis and trans isomers of example 37 as shown below:

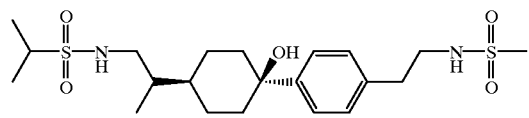
Example 37; Cis

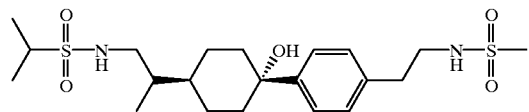
Example 37; Trans are included within the scope of the present invention.

In addition, the corresponding individual regioisomers of the above examples, wherein the phenyl group can be substituted in the ortho or meta position, are included within the scope of the present invention. For example, the following individual ortho and meta regioisomers of example 28 are included within the scope of the present invention.

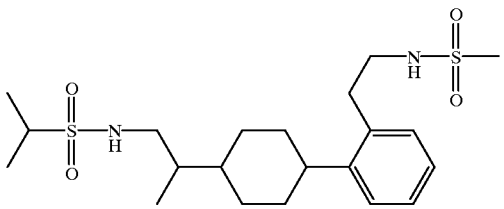
ortho-substituted

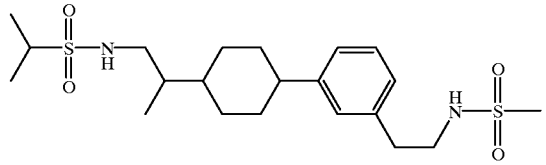
meta-substituted

The following Table II provides additional compounds according to the present invention. The following compounds can be prepared by one of ordinary skill in the art utilizing procedures and techniques described hereinabove. The starting materials and reagents are available to one of ordinary skill in the art.

TABLE II

| Example | Compound |
|---|---|
| 155 | (structure: isopropylsulfonamide-CH2-CH(CH3)-cyclohexyl-C6H4-CN (para)) |
| 156 | (structure: isopropylsulfonamide-CH2-CH(CH3)-cyclohexyl(OH)-C6H4-CN (para)) |
| 157 | (structure: isopropylsulfonamide-CH2-CH(CH3)-cyclohexyl-C6H4-CN (meta)) |
| 158 | (structure: isopropylsulfonamide-CH2-CH(CH3)-cyclohexenyl-C6H4-CN (meta)) |
| 159 | (structure: isopropylsulfonamide-CH2-CH(CH3)-cyclohexyl(OH)-C6H4-CN (meta)) |
| 160 | (structure: isopropylsulfonamide-CH2-CH(CH3)-cyclohexyl-C6H4-CN (ortho)) |
| 161 | (structure: isopropylsulfonamide-CH2-CH(CH3)-cyclohexenyl-C6H4-CN (ortho)) |
| 162 | (structure: isopropylsulfonamide-CH2-CH(CH3)-cyclohexyl(OH)-C6H4-CN (ortho)) |
| 163 | (structure: isopropylsulfonamide-CH2-CH(CH3)-cyclohexyl-C6H4-CH2CO2H (para)) |

TABLE II-continued
| Example | Compound |
|---|---|
| 164 | 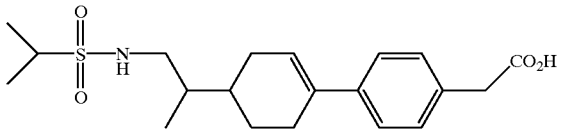 |
| 165 | 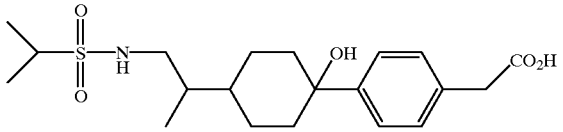 |
| 166 | 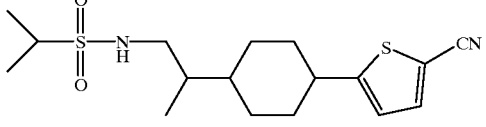 |
| 167 | 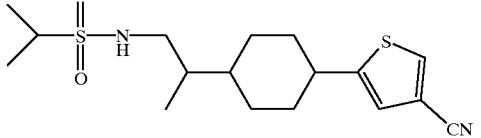 |
| 168 | 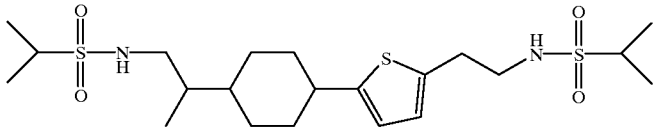 |
| 169 | 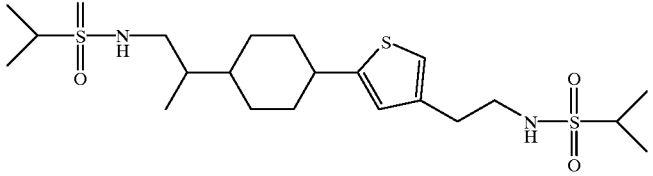 |
| 170 | 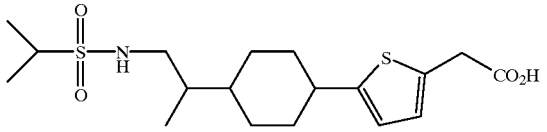 |
| 171 | 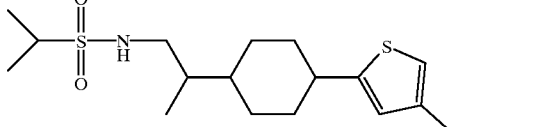 |

What is claimed is:

1. A compound of the formula:

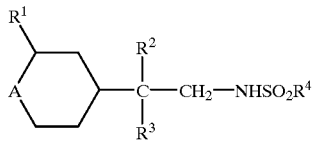

in which:

A represents $CR^5(X^1R^6)$ or $C=NO(CH_2)_nR^7$;

$R^1$ represents hydrogen, or together with $R^5$ a bond;

$R^2$ and $R^3$ each independently represents hydrogen or (1–4C)alkyl, or together with the carbon atom to which they are attached form a (3–6C)cycloalkyl ring;

$R^4$ represents (1–6C)alkyl, (3–6C)cycloalkyl, fluoro (1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C) alkoxy, (1–4C)alkylphenyl wherein the phenyl group is unsubstituted or substituted by halogen, (1–4C)alkyl or (1–4C)alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group;;

$R^5$ represents hydrogen, hydroxy, (1–4C)alkoxy, (1–4C) alkoxycarbonyl, or together with a substituent on $R^6$ a bond, or together with $R^1$ a bond;

$X^1$ represents a bond, or when $R^1$ represents hydrogen, NHCO;

$R^6$ represents (3–8C)cycloalkyl or an unsubstituted or substituted aromatic or heteroaromatic group;

n is an integer of from 1 to 4; and $R^7$ is as defined for $R^6$;

or a pharmaceutically acceptable salt thereof.

2. A compound as claimed in claim 1, in which $R^2$ and $R^3$ each independently represents hydrogen or methyl.

3. A compound as claimed in claim 2, in which $R^2$ represents methyl and $R^3$ represents hydrogen.

4. A compound as claimed in claim 3, in which $R^4$ represents ethyl, isopropyl or dimethylamino.

5. A compound as claimed in claim 4, in which $R^4$ represents isopropyl.

6. A compound as claimed in claim 1, in which $R^6$ represents cyclopentyl, or a furyl, thienyl, thiazolyl, pyridyl or phenyl group which is unsubstituted or substituted with one or two substituents selected independently from halogen; amino; cyano; formyl; carboxy; nitro; (1–4C)alkyl; (2–4C)alkenyl; (2–4C)alkynyl; halo(1–4C)alkyl; cyano (1–4C)alkyl; amino(1–4C)alkyl; (1–4C)alkyl-$NHSO_2R^{17}$; (1–4C)alkyl-$CO_2R^{18}$; (1–4C)alkyl-$CO_2H$; (1–4C)alkyl-$CONR^9R^{10}$; (3–8C)cycloalkyl; 2,5-dimethylpyrrolyl; wherein $R^{17}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C) alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; $R^{18}$ represents 1–6C)alkyl, (3–6C)cycloalkyl, fluoro(1–6C)alkyl, chloro (1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, and groups of formula $(L^1)_x$—$X^2$—$(L^1)_y$—$R^{11}$ in which each of $L^1$ and $L^2$ independently represents (1–4C)alkylene, one of x and y is 0 and the other is 0 or 1, $X^2$ represents a bond, O, S, NH, CO, CONH or NHCO, and $R^{11}$ represents a furyl, thienyl, thiazolyl, pyridyl or phenyl group which is unsubstituted or substituted by one or two of halogen, (1–4C)alkyl and (1–4C)haloalkyl.

7. A compound as claimed in claim 6, in which $R^6$ represents a group of formula

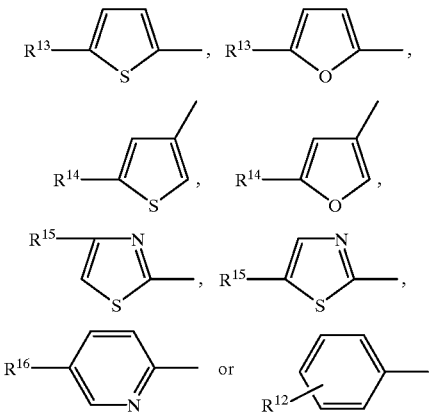

in which $R^{12}$, $R^{13}$, $R^{14}$, $R^{15}$ and $R^{16}$ represent halogen, amino, cyano, formyl, nitro, (1–4C)alkyl, (2–4C)alkenyl, (2–4C)alkynyl, halo(1–4C)alkyl, cyano(1–4C)alkyl, amino (1–4C)alkyl, (1–4C)alkyl-$NHSO_2R^{17}$, (3–8C)cycloalkyl, wherein $R^{17}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C) alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; or a group of formula $(L^1)_x$—$X^2$—$(L^1)_y$—$R^{11}$.

8. A compound as claimed in claim 7, in which $R^6$ represents cyclopentyl, thien-2-yl, thien-3-yl, fur-3-yl, 5-(pyrid-2-yl)thien-2-yl, thiazol-2-yl, pyrid-2-yl, phenyl, 4-formylphenyl, 4-aminophenyl, 4-cyanophenyl, 4-cyanomethylphenyl, 4-aminomethylphenyl, 4-isopropylsulfonylaminomethylphenyl, 4-methylsulfonylaminoethylphenyl, or 4-(2,5-dimethylpyrrolyl)phenyl; or together with $R^5$ and the carbon atom to which it is attached is spiroisobenzofuranyl.

9. A compound as claimed in claim 1, in which A represents $CR^5(X^1R^6)$.

10. A compound which is N-[2-[4-(4-methanesulfonylaminoethylphenyl)-3-cyclohexan-1-yl] propyl 2-propanesulfonamide.

11. A pharmaceutical composition, which comprises a compound as claimed in claim 1 and a pharmaceutically acceptable diluent or carrier.

12. A method of potentiating glutamate receptor function in a warm blooded mammal requiring treatment which comprises administering an effective amount of a compound as claimed in claim 1.

13. A compound of formula

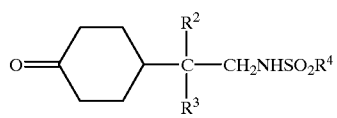

IV in which $R^2$ and $R^3$ each independently represents hydrogen or (1–4C)alkyl, or together with the carbon atom to which they are attached form a (3–6C)cycloalkyl ring; and $R^4$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; or a salt thereof.

14. A compound of the formula:

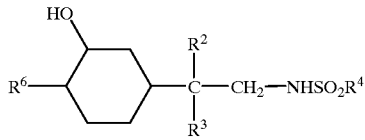

in which
$R^2$ and $R^3$ each independently represents hydrogen or (1–4C)alkyl, or together with the carbon atom to which they are attached form a (3–6C)cycloalkyl ring;

$R^4$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; and $R^6$ represents (3–8C)cycloalkyl or an unsubstituted or substituted aromatic or heteroaromatic group;
or a pharmaceutically acceptable salt thereof.

15. A compound as claimed in claim 14, in which $R^2$ and $R^3$ each independently represents hydrogen or methyl.

16. A compound as claimed in claim 15, in which $R^2$ represents methyl and $R^3$ represents hydrogen.

17. A compound as claimed in claim 16, in which $R^4$ represents ethyl, isopropyl or dimethylamino.

18. A compound as claimed in claim 17, in which $R^4$ represents isopropyl.

19. A compound as claimed in claim 14, in which $R^6$ represents cyclopentyl, or a furyl, thienyl, thiazolyl, pyridyl or phenyl group which is unsubstituted or substituted with one or two substituents selected independently from halogen; amino; cyano; formyl; carboxy; nitro; (1–4C)alkyl; (2–4C)alkenyl; (2–4C)alkynyl; halo(1–4C)alkyl; cyano(1–4C)alkyl; amino(1–4C)alkyl; (1–4C)alkyl-$NHSO_2R^{17}$; (1–4C)alkyl-$CO_2R^{18}$; (1–4C)alkyl-$CO_2H$; (1–4C)alkyl-$CONR^9R^{10}$; (3–8C)cycloalkyl; 2,5-dimethylpyrrolyl; wherein $R^{17}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; $R^{18}$ represents 1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, and groups of formula $(L^1)_x$—$X^2$—$(L^1)_y$—$R^{11}$ in which each of $L^1$ and $L^2$ independently represents (1–4C)alkylene, one of x and y is 0 and the other is 0 or 1, $X^2$ represents a bond, O, S, NH, CO, CONH or NHCO, and $R^{11}$ represents a furyl, thienyl, thiazolyl, pyridyl or phenyl group which is unsubstituted or substituted by one or two of halogen, (1–4C)alkyl and (1–4C)haloalkyl.

20. A compound as claimed in claim 19, in which $R^6$ represents a group of formula

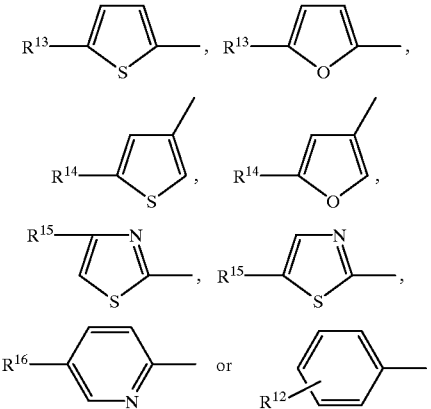

in which $R^{12}$, $R^{13}$, $R^{14}$, $R^{15}$ and $R^{16}$ represent halogen, amino, cyano, formyl, nitro, (1–4C)alkyl, (2–4C)alkenyl, (2–4C)alkynyl, halo(1–4C)alkyl, cyano(1–4C)alkyl, amino(–4C)alkyl, (1–4C)alkyl-$NHSO_2R^{17}$, (3–8C)cycloalkyl, wherein $R^{17}$ represents (1–6C)alkyl, (3–6C)cycloalkyl, fluoro(1–6C)alkyl, chloro(1–6C)alkyl, (2–6C)alkenyl, (1–4C)alkoxy(1–4C)alkyl, phenyl which is unsubstituted or substituted by halogen, (1–4C)alkyl or (1–4C)alkoxy, (1–4C)alkylphenyl wherein the phenyl group is unsubstituted or substituted by halogen, (1–4C)alkyl or (1–4C)alkoxy, or $NR^9R^{10}$ in which each of $R^9$ and $R^{10}$ independently represents (1–4C)alkyl or together with the nitrogen atom to which they are attached form an azetidinyl, pyrrolidinyl, piperidinyl, morpholino, piperazinyl, hexahydroazepinyl or octahydroazocinyl group; or a group of formula $(L^1)_x$—$X^2$—$(L^1)_y$—$R^{11}$.

21. A compound as claimed in claim 20, in which $R^6$ represents cyclopentyl, thien-2-yl, thien-3-yl, fur-3-yl, 5-(pyrid-2-yl)thien-2-yl, thiazol-2-yl, pyrid-2-yl, phenyl, 4-formylphenyl, 4-aminophenyl, 4-cyanophenyl, 4-cyanomethylphenyl, 4-aminomethylphenyl, 4-isopropylsulfonylaminomethylphenyl, 4-methylsulfonylaminoethylphenyl, or 4-(2,5-dimethylpyrrolyl)phenyl; or together with $R^5$ and the carbon atom to which it is attached is spiroisobenzofuranyl.

22. A pharmaceutical composition, which comprises a compound as claimed in claim 14 and a pharmaceutically acceptable diluent or carrier.

23. A method of potentiating glutamate receptor function in a warm blooded mammal requiring treatment which comprises administering an effective amount of a compound as claimed in claim 14.

\* \* \* \* \*